(12) United States Patent
Park et al.

(10) Patent No.: US 7,541,100 B2
(45) Date of Patent: Jun. 2, 2009

(54) ORGANIC METAL COMPOUNDS IN WHICH COMPOUNDS FOR HOST AND COMPOUNDS FOR DOPANT ARE CONNECTED, ORGANIC ELECTROLUMINESENCE DISPLAY DEVICES USING THE COMPOUNDS AND METHOD FOR PREPARATION OF THE DEVICES

(76) Inventors: Soo Jin Park, Daewoo Apt. 103-502, Daushipril - dong, Dongdaemon-gu, Seoul (KR); Dae Yup Shin, 102, 528-2 Wooman 1-dong, Paldai-gu, Suwon-si, Gyeonggi-do (KR); Dong Hyun Jung, Jeogong Apt. 401-906, 300 Wooman-dong, Paldai-gu, Suwon-si (KR); Tae Hyuk Kwon, Samick Apt. 405-108, Suseo-dong, Kangnam-gu, Seoul (KR); Myoung Ki Kim, 203-56 Shinback-ding, Jechun-si, Chungcheongbuck-do (KR); Jong In Hong, Hyundai Apt. 107-1004, Shinrion 2-dong, Kwanack-gu, Seoul (KR)

( * ) Notice: Subject to any disclaimer, the term of this patent is extended or adjusted under 35 U.S.C. 154(b) by 486 days.

(21) Appl. No.: 11/364,521

(22) Filed: Feb. 27, 2006

(65) Prior Publication Data
US 2006/0237715 A1    Oct. 26, 2006

(30) Foreign Application Priority Data
Apr. 21, 2005    (KR) .................... 10-2005-0033083

(51) Int. Cl.
*H01L 51/54* (2006.01)
*C09K 11/06* (2006.01)

(52) U.S. Cl. ............ 428/690; 428/917; 313/504; 313/506; 257/40; 257/E51.044; 546/4; 548/440

(58) Field of Classification Search .................... None
See application file for complete search history.

(56) References Cited

U.S. PATENT DOCUMENTS
6,303,238 B1    10/2001    Thompson et al.
(Continued)

FOREIGN PATENT DOCUMENTS
WO    WO 03/001616 A2    1/2003
(Continued)

OTHER PUBLICATIONS

You et al. (2006) Blue electrophosphorescence from iridium complex covalently bonded to the poly(9-dodecyl-3-vinylcarbazole): suppressed phase segregation and enhanced energy transfer. Macromolecules. 39:349-356.
(Continued)

*Primary Examiner*—Marie R. Yamnitzky
(74) *Attorney, Agent, or Firm*—Knobbe Martens Olson & Bear, LLP

(57) ABSTRACT

Organic metal compounds in which compounds for host and compounds for dopant are connected, organic electroluminescence display devices using the compounds and a method for preparation of the devices are disclosed. Also disclosed are organic metal compounds in which the compounds for host and the compounds for dopant are connected to make energy transmission between host and dopant possible in a molecular level, organic electroluminescence display devices using the same and a preparation method thereof.

12 Claims, 6 Drawing Sheets

U.S. PATENT DOCUMENTS

| | | |
|---|---|---|
| 2001/0053463 A1 | 12/2001 | Thompson et al. |
| 2002/0034656 A1 | 3/2002 | Thompson et al. |
| 2002/0121638 A1 | 9/2002 | Grushin et al. |
| 2003/0091862 A1 | 5/2003 | Tokito et al. |
| 2004/0121184 A1 | 6/2004 | Thompson et al. |
| 2004/0219387 A1 * | 11/2004 | Li et al. ............... 428/690 |
| 2004/0253478 A1 | 12/2004 | Thompson et al. |
| 2005/0031903 A1 | 2/2005 | Park et al. |

FOREIGN PATENT DOCUMENTS

WO    WO 03/079736    *    9/2003

OTHER PUBLICATIONS

Courtesy copy of European Search Report in 3 pages. Jun. 22, 2006.

* cited by examiner

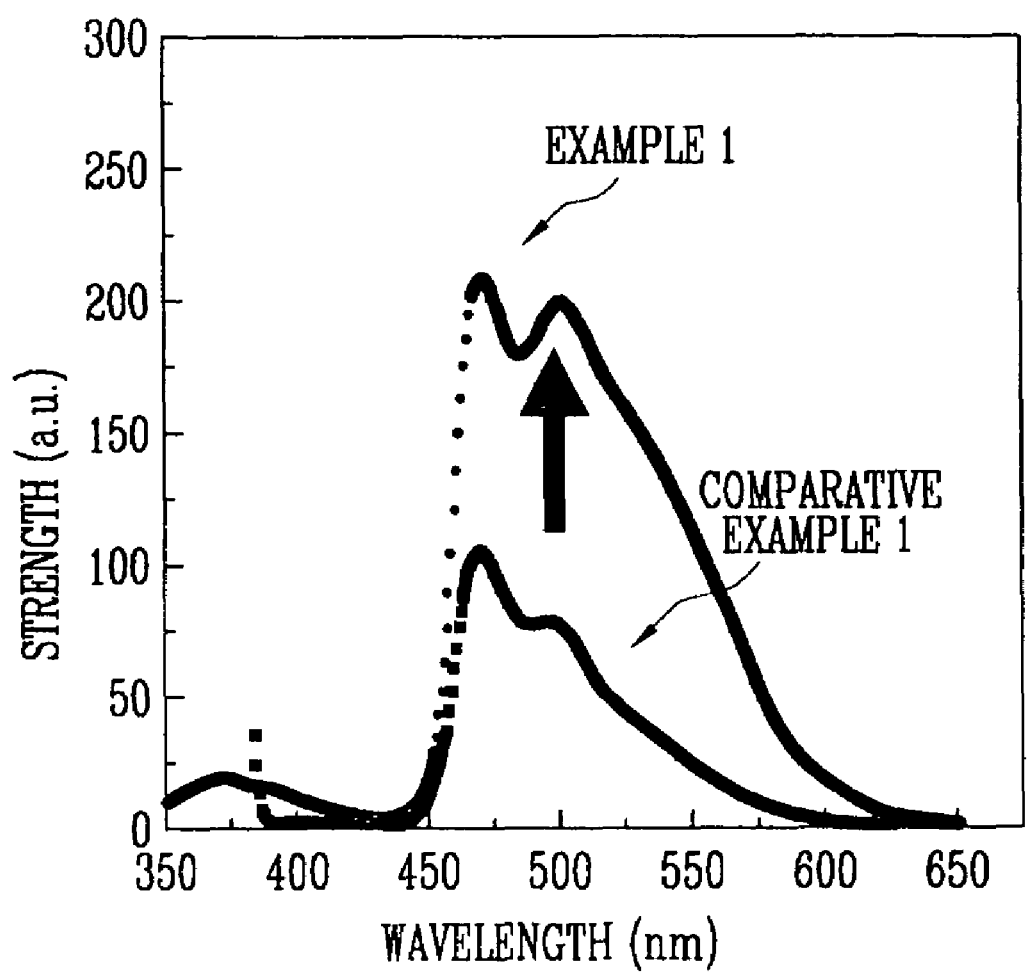

ORGANIC METAL COMPOUNDS IN WHICH COMPOUNDS FOR HOST AND COMPOUNDS FOR DOPANT ARE CONNECTED, ORGANIC ELECTROLUMINESENCE DISPLAY DEVICES USING THE COMPOUNDS AND METHOD FOR PREPARATION OF THE DEVICES

CROSS-REFERENCE TO RELATED APPLICATIONS

This application claims the benefit of Korean Patent Application No. 10-2005-0033083 filed on Apr. 21, 2005, in the Korean Intellectual Property Office, the disclosure of which is incorporated herein by reference.

BACKGROUND OF THE INVENTION

1. Field of the Invention

The present embodiments relate to organic metal compounds in which compounds for host and compounds for dopant are connected, organic electroluminescence display devices using the compounds and a method for preparation of the devices. More precisely, the present embodiments relate to organic metal compounds in which compounds for host and compounds for dopant are connected to make energy transmission between host and dopant possible on a molecular level, organic electroluminescence display devices using the same and a preparation method thereof.

2. Description of the Related Art

As a self-emissive display device, electroluminescence display devices (EL devices) have a broad visual angle, excellent contrast, and a quick response time.

EL devices are divided into inorganic EL devices and organic EL devices according to the emitting layer forming materials. Organic EL devices have advantages over inorganic EL devices such as excellent brightness and driving voltage, a quick response time, and polychromy.

In general, in the structure of an organic EL device comprises anodes formed on a substrate, and in the upper part of the anode, a hole transport layer, an emitting layer, an electron transport layer and a cathode are formed in that order. The hole transport layer, emitting layer, and electron transport layer are organic thin films composed of organic compounds.

The drive principal of organic EL devices having the above structure is as follows.

Once voltage is applied between the anode and the cathode, holes are infused from the anode into the emitting layer via a hole transport layer. In the meantime, electrons are infused into the emitting layer from a cathode via an electron transport layer. In the region of the emitting layer, carriers are rearranged to form exitons. The excited exiton is transformed into ground state, resulting in emission of the emitting layer molecules. As a result, images are formed. Emitting materials are classified according to emitting mechanism into two groups; one is composed of fluorescent materials using exitons in the state of singlet, and the other group is composed of phosphorescent substances using exitons in the state of triplet.

Phosphorescent substances have an organomineral compound structure containing generally heavy atoms, by which an exiton can be transformed from the state of triplet, a forbidden transition, through allowed transition. Phosphorescent substances have much higher emitting efficiency by using triplet exiton, having 75% generation ratio, than fluorescent materials which use singlet exiton with 25% generation ratio.

An emitting layer formed by phosphorescent substances is composed of a host material and a dopant material which is luminous by energy transmission from the host material. Dopant materials include various iridium metal compounds.

As a part of study on organic electroluminescent materials using iridium compounds, research teams at Princeton University and University of Southern California reported phosphorescent substances based on iridium, and platinum metal compounds. But more studies are ongoing to develop a better luminous stable material.

While a low molecular weight organic EL material must be formed by using a dry process such as vacuum deposition, a high molecular weight EL material can be formed by using a wet process such as spin coating, etc. The low molecular weight EL material cannot be formed by a wet process because of its low solubility. Although the high molecular weight EL material has a solubility high enough to form a device by wet process, it has a low emission property, in particular, a shorter lifetime than the low molecular weight EL material. Thus, it is required to develop an organic EL material having high solubility to form a device by wet process, an easier and more economical process than deposition, and at the same time having emission properties as high as a low molecular EL material.

SUMMARY OF THE INVENTION

It is an object of the present embodiments to provide an organic metal compound in which compounds for host and compounds for dopant are connected.

It is another object of the present embodiments to provide an organic electroluminescence device using the organic metal compound in which compounds for host and compounds for dopant are connected.

It is a further object of the present embodiments to provide a preparation method of the organic electroluminescence device using the organic metal compound in which compounds for host and compounds for dopant are connected.

In order to achieve the first object of the embodiments, the present embodiments provide an organic metal compound of the following formula 1 in which compounds for host and compounds for dopant are connected.

Formula 1

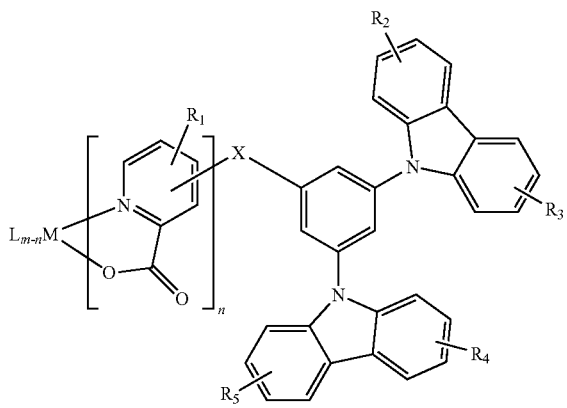

wherein, X has one of the following structures;

X1:

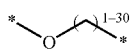

X2:

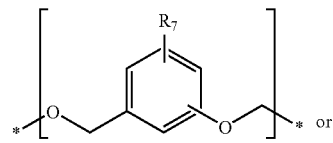

or

-continued

X3:
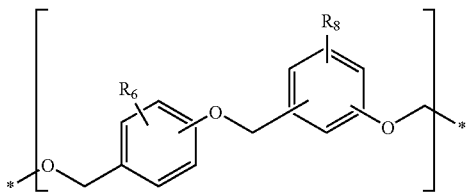

wherein, $R_1$-$R_8$ are each independently mono-substituted or multi-substituted functional groups selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(R')(R")(R''') wherein, R', R" and R''' are independently H or $C_1$-$C_{30}$ alkyl, and —N(R')(R") wherein R' and R" are independently H or $C_1$-$C_{30}$ alkyl, and the neighboring groups among functional groups of $R_1$-$R_8$ can be linked to each other to form a ring;

wherein M can be Ir, Os, Pt, Pb, Re or Ru; and

L is a bidentate ligand, m is 3, and n is 1 or 2.

In order to achieve the second object of the embodiments, the present embodiments provide an organic electroluminescence device comprising a pair of electrodes and an organic layer between the pair of electrodes that contain organic metal compounds of the formula I in which compounds for host and compounds for dopant are connected.

In order to achieve the third object of the embodiments, the present embodiments provide a preparation method for an organic electroluminescence device comprising the following steps: forming a first electrode on substrate; forming an organic layer on the first electrode; and forming a second electrode on the organic layer, wherein the organic layer is formed by doping of organic metal compounds of the formula 1 in which compounds for host and compounds for dopant are connected.

BRIEF DESCRIPTION OF THE DRAWINGS

These and/or other aspects and advantages of the embodiments will become apparent and more readily appreciated from the following description of the preferred embodiments, taken in conjunction with the accompanying drawings of which:

FIG. 5 is a graph showing the comparison of PL spectra in chloroform solution between the compound of formula 7 synthesized in Example 1 and the compound of formula 16 synthesized in Comparative Example 1.

DETAILED DESCRIPTION OF PREFERRED EMBODIMENTS

Figure 1:
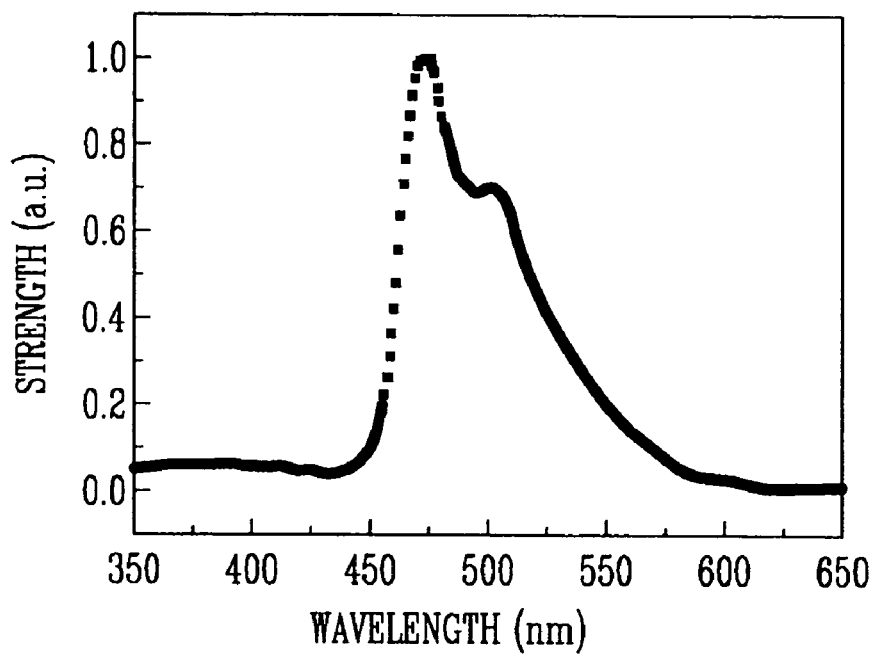
FIG. 1 is a graph showing a PL (photoluminescence) spectrum in THF solution of the compound represented by formula 7, synthesized in Example 1.

Hereinafter, preferable embodiments according to the present embodiments will be described with reference to the accompanying drawings, wherein preferred embodiments are provided to be readily understood by those skilled in the art.

The organic metal compound represented by the following formula 1 according to the present embodiments is a compound in which compounds for host are connected to compounds for dopant.

Formula 1

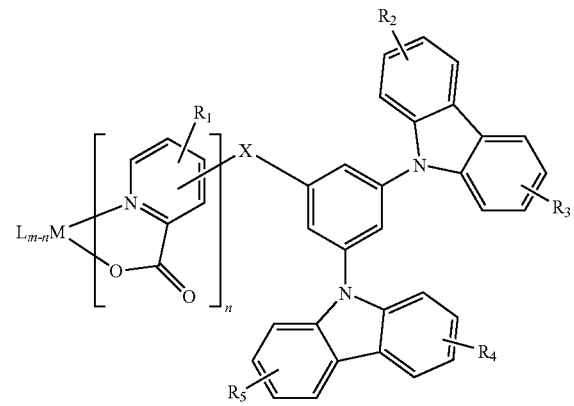

wherein X has one of the following structures;

X1:
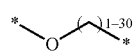

X2:
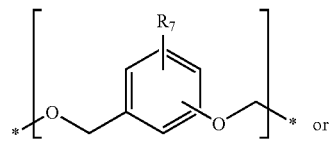 or

X3:
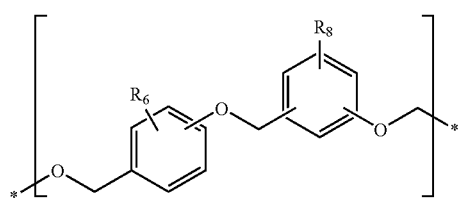

$R_1$-$R_8$ are each independently mono-substituted or multi-substituted functional groups selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(R')(R'')(R''') wherein R', R'' and R''' are independently H or $C_1$-$C_{30}$ alkyl, and —N(R')(R'') wherein R' and R'' are independently H or $C_1$-$C_{30}$ alkyl, and the neighboring groups among functional groups of $R_1$-$R_8$ can be linked to each other to form a ring;

M can be Ir, Os, Pt, Pb, Re or Ru; and

L is bidentate ligand, m is 3, and n is 1 or 2.

The organic metal compound of formula 1 of the present embodiments is prepared by connecting compounds for dopant with compounds for host having the same or different energy gap between HOMO (Highest Occupied Molecular Orbital)—LUMO (Lowest Unoccupied Molecular Orbital). The energy gap of compounds for host should be identical to or different from that of compounds for dopant, and preferably the energy gap between compounds for host and compounds for dopant should be from about 0 to about 400 nm. The resultant organic metal compound in which compounds for host and compounds for dopant are connected not only shows excellent emission properties but also increases the molecular weight, resulting in the enhanced solubility.

The organic metal compounds of the present-embodiments have a structure in which compounds for host and compounds for dopant are connected by a linker. And several compounds for the host can be connected to a compound for the dopant according to the kinds of linkers.

The linker should be a moiety capable of breaking p-conjugation between compounds for host and compounds for dopant, and should be a moiety having a multifunctional group which does not disturb energy transmission between molecules for host and molecules for dopant. For example, a moiety containing an oxygen atom is preferred. Specifically, hydroquinone, 3,5-dihydroxybenzylalcohol and the like can be used as a linker.

As explained above, the number of compounds for host to be conjugated to a compound for dopant is regulated by a connecter, leading to the regulation of doping concentration for an organic electroluminescence device. More specifically, it is preferred for a connecter to have X1, X2 or X3 in the formula 1.

The compound of the present embodiments, represented by formula 1, has one of the representative structures of the following formulae 2-4, according to a linker X.

Compounds of formula 2 have X1 in the position of X of the above formula 1. Formula 2 is set forth below:

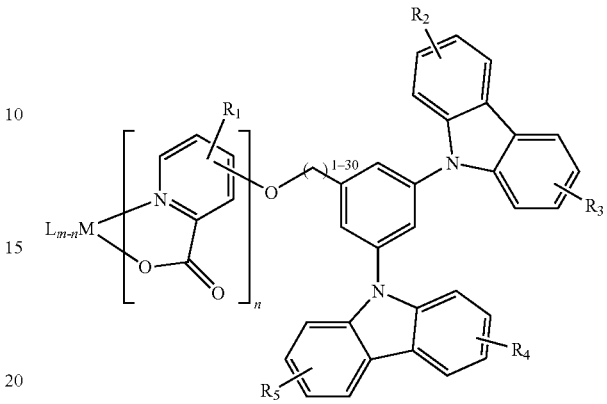

Formula 2 wherein, $R_1$-$R_5$ are each independently mono-substituted or multi-substituted functional groups selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(R')(R'')(R''') wherein R', R'' and R''' are independently H or $C_1$-$C_{30}$ alkyl, and —N(R')(R'') wherein R' and R'' are independently H or $C_1$-$C_{30}$ alkyl, and the neighboring groups among functional groups of $R_1$-$R_8$ can be linked to each other to form a ring;

M can be Ir, Os, Pt, Pb, Re or Ru; and

L is bidentate ligand, m is 3, and n is 1 or 2.

Compounds of formula 3 have X2 in the position of X of the above formula 1. Formula 3 is set forth below:

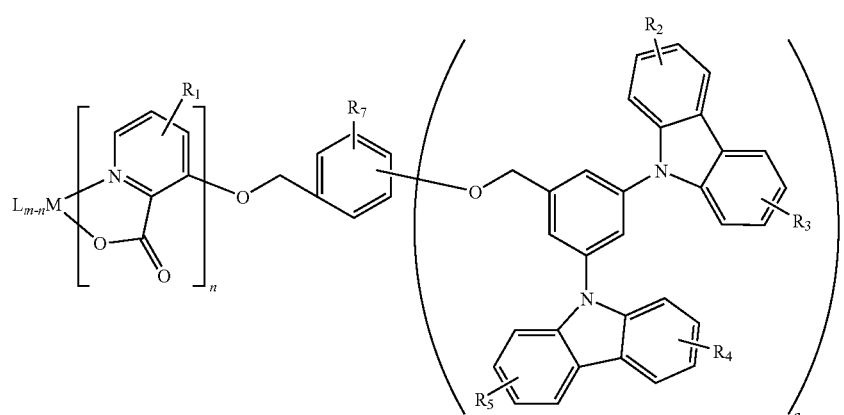

Formula 3 wherein, $R_1$-$R_5$ and $R_7$ are each independently mono-substituted or multi-substituted functional groups selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(R')(R'')(R''') wherein R', R'' and R''' are independently H or $C_1$-$C_{30}$ alkyl, and —N(R')(R'') wherein R' and R'' are independently H or $C_1$-$C_{30}$ alkyl, and the neighboring groups among functional groups of $R_1$-$R_8$ can be linked to each other to form a ring;

M can be Ir, Os, Pt, Pb, Re or Ru; and

L is bidentate ligand, m is 3, and n is 1 or 2; and a is 1, 2 or 3.

Compounds of formula 4 is a compound having X3 in the position of X of the above formula 1. Formula 4 is set forth below:

selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(R')(R'')(R''') wherein R', R'' and R''' are independently H or $C_1$-$C_{30}$ alkyl, and —N(R')(R'') wherein R' and R'' are independently H or $C_1$-$C_{30}$ alkyl, and the neighboring groups among functional groups of $R_1$-$R_8$ can be linked to each other to form a ring;

M can be Ir, Os, Pt, Pb, Re or Ru; and

L is bidentate ligand, m is 3, and n is 1 or 2; and a is 1, 2 or 3.

Preferred structures of the luminescent compound portion of the compounds of Formula 1 (that is, without the binding ligand portion) are as follows:

Formula 4

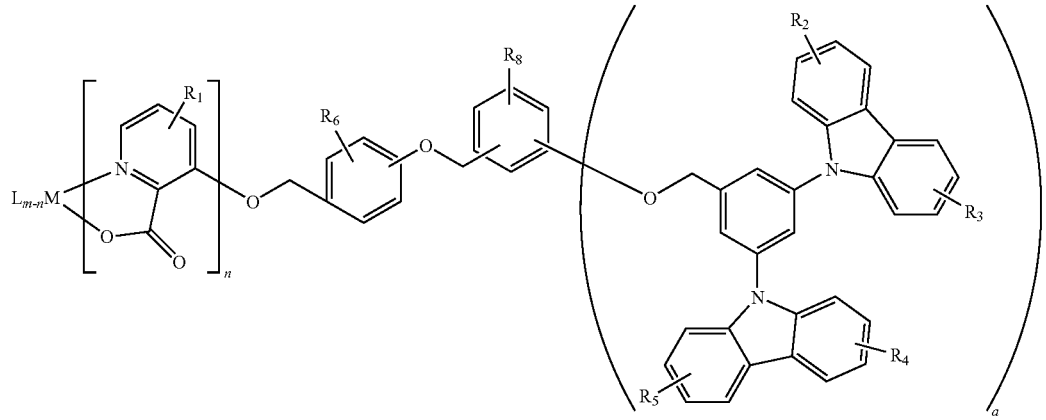

wherein, $R_1$-$R_5$, $R_6$ and $R_8$ are are each independently mono-substituted or multi-substituted functional groups Formula 5

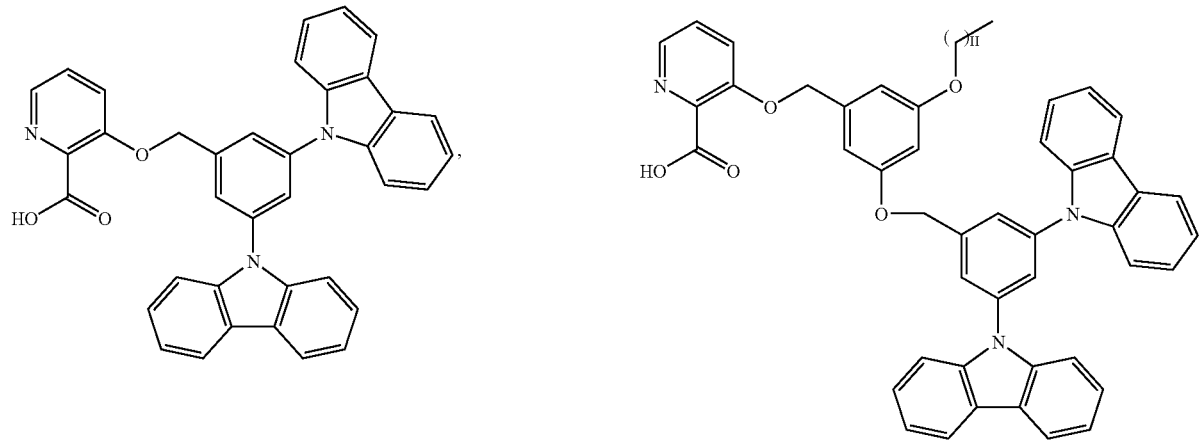

-continued
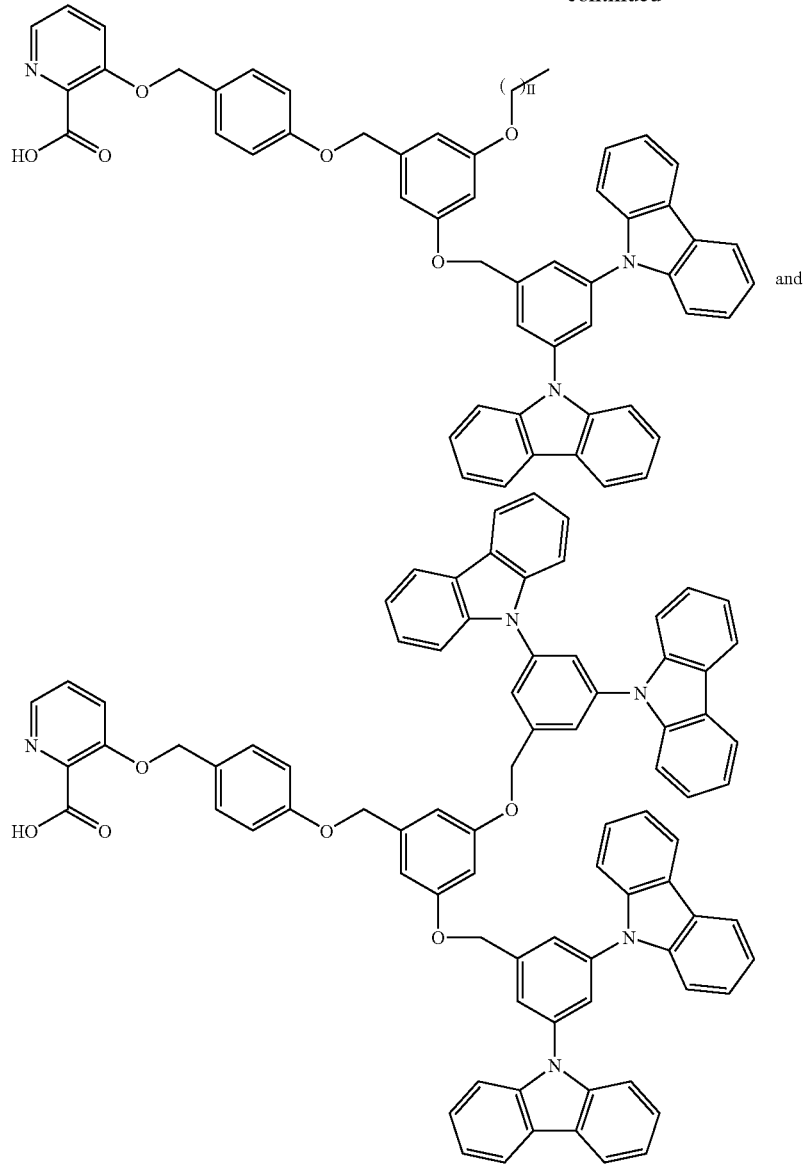
Examples of L in the compound of formula 1 of the present embodiments include but are not limited to those having the structure represented by the following:
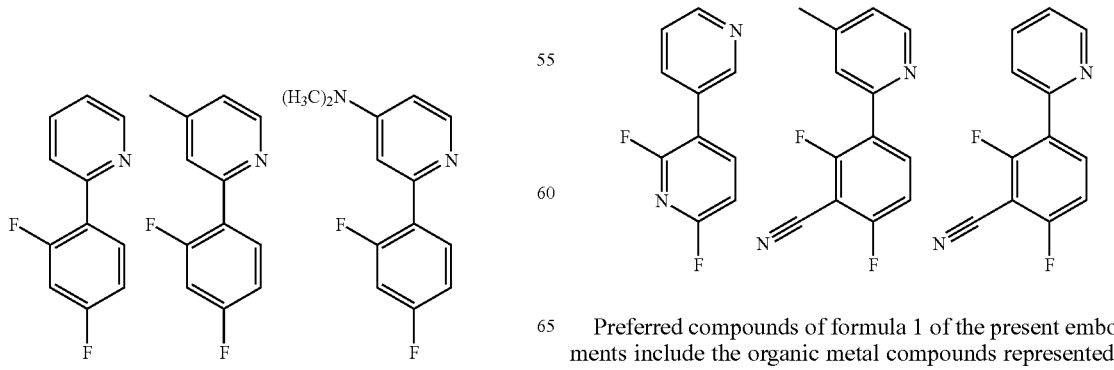
Preferred compounds of formula 1 of the present embodiments include the organic metal compounds represented by formulae 7-15.

Formula 7
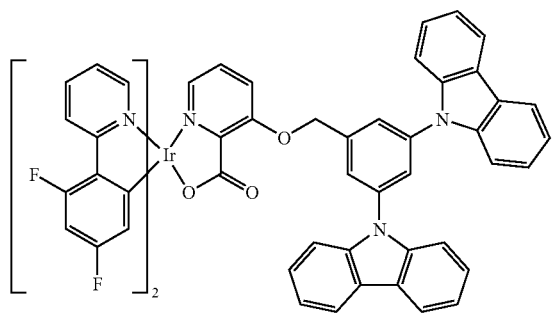
Formula 8
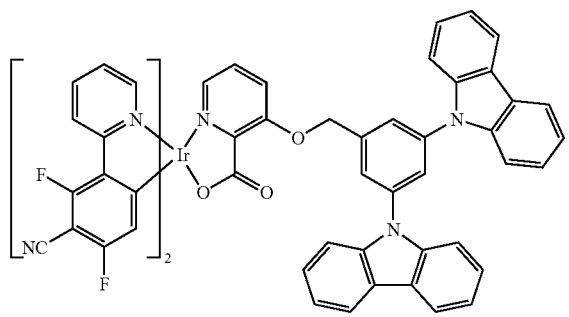
Formula 9
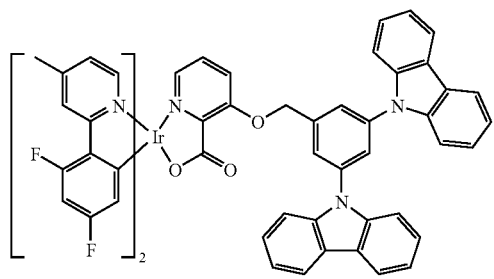
Formula 10
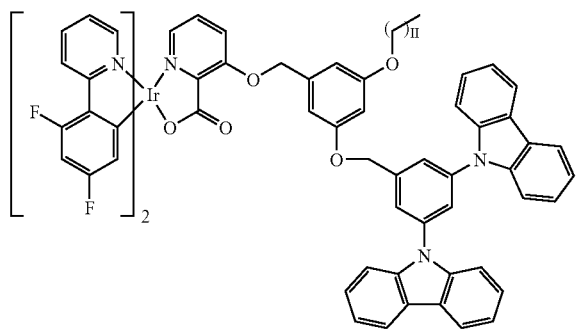
Formula 11
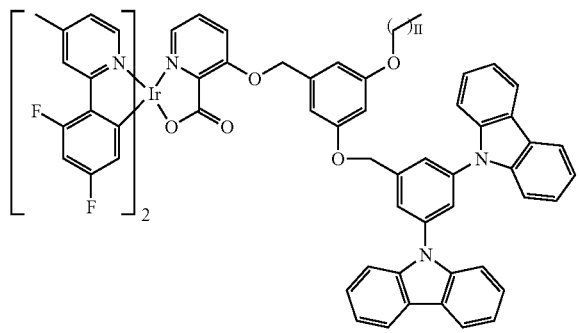
Formula 12
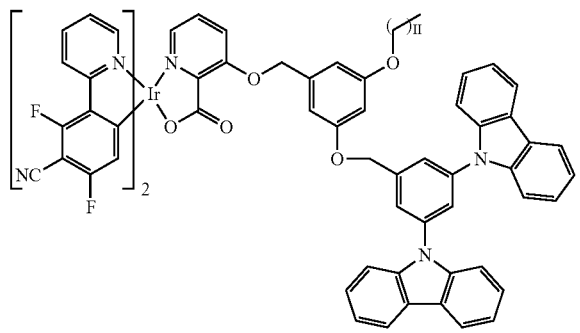
Formula 13
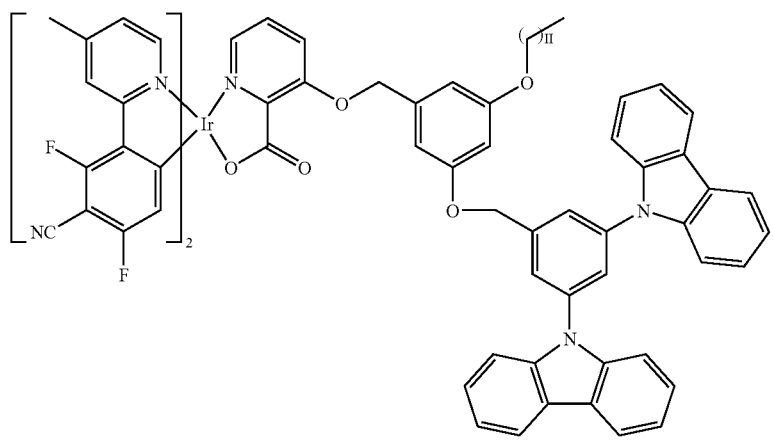

Formula 14

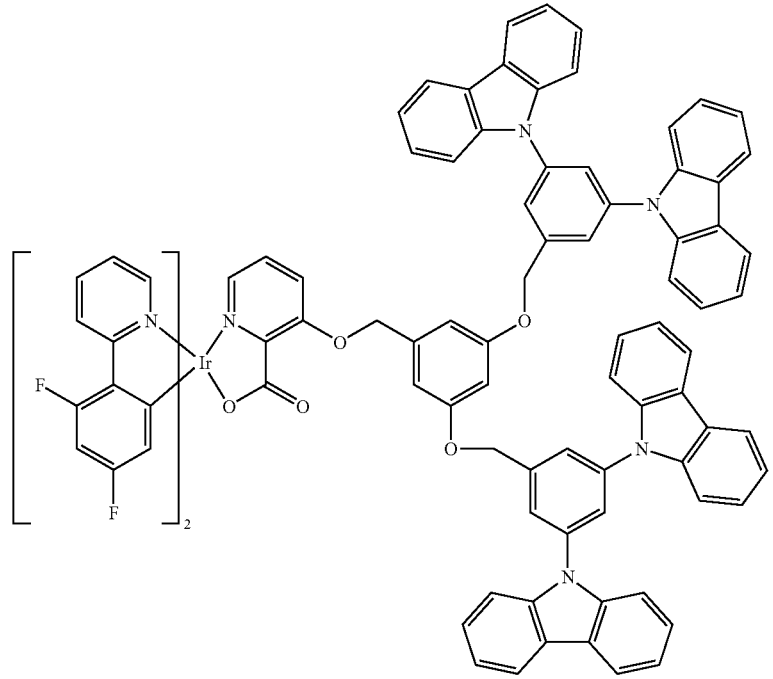

Formula 15

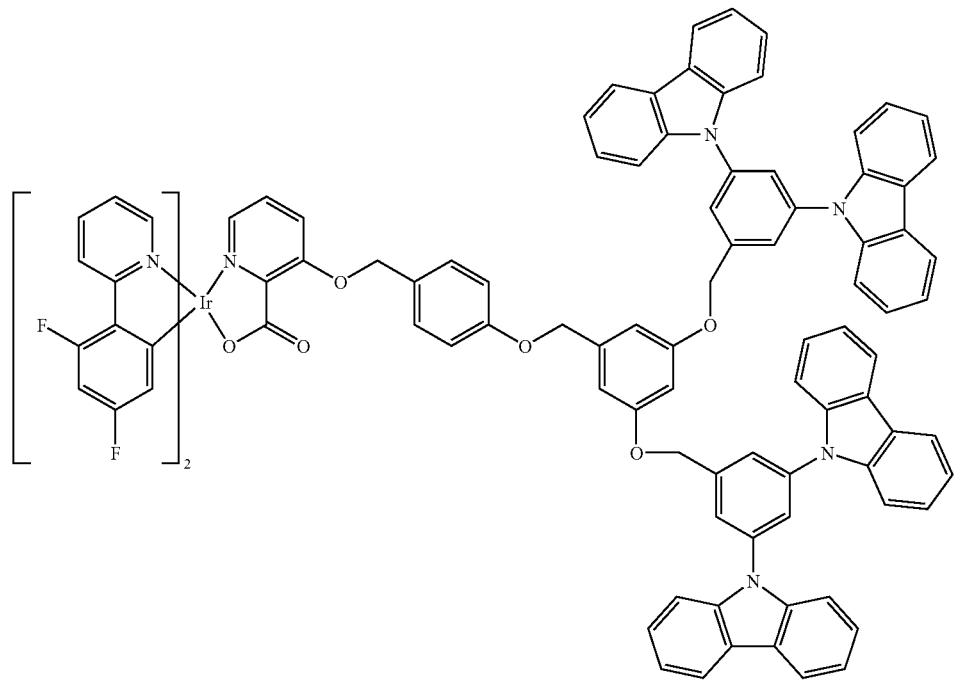

As used herein, the terms, "nonsubstituted alkyl" or "nonsubstituted alkoxy" means the alkyl having 1-30 carbons (for example, methyl, ethyl, propyl, butyl, pentyl, hexyl, octyl, nonyl, decyl, undecyl, dodecyl, tridecyl, tetradecyl, pentadecyl, etc, or their isomers); and the terms "substituted alkyl" or "substituted alkoxy" means that at least one hydrogen atom of the nonsubstituted alkyl part is replaced with, for example, halogen atom, hydroxy, nitro, cyano, amino, amidino, hydrazine, hydrazone, carboxyl or its salt, sulfonic acid or its salt, phosphoric acid or its salt, $C_1$-$C_{30}$ alkyl, $C_2$-$C_{30}$ alkenyl, $C_2$-$C_{30}$ alkynyl, $C_6$-$C_{30}$ aryl, $C_7$-$C_{30}$ arylalkyl, $C_2$-$C_{20}$ heteroaryl, or $C_3$-$C_{30}$ heteroalkyl.

"Nonsubstituted alkenyl" means $C_2$-$C_{30}$ alkenyl which has at least one double bond (for example, ethene, protene, butene, pentene, hexene, etc, or their isomers), and "substituted alkenyl" indicates that at least one hydrogen atom of the nonsubstituted alkenyl above is replaced one selected from the same groups of substituents as described above in the case of alkyl.

"Nonsubstituted aryl" indicates aromatic carbon rings having 6-30 carbons, forming one or more rings singly or together. The rings can be attached or fused together by pendant method. "Substituted aryl" indicates that any one of hydrogen atoms of nonsubstituted aryl is replaced with one selected from the same group of substituents as described in the case of alkyl.

"Nonsubstituted arylalkyl" indicates that at least one hydrogen atom of aryl is replaced with one lower alkyl group such as methyl, ethyl, propyl, etc. "Substituted arylalkyl" indicates that at least one hydrogen atom of the nonsubstituted arylalkyl is replaced with one selected from the same group of substituents as described in the case of alkyl.

"Nonsubstituted aryloxy" indicates that at least one hydrogen atom of aryl is replaced with an oxygen atom, which is exemplified by phenyloxy, naphthyleneoxy, diphenyloxy, etc. "Substituted aryloxy" indicates that at least one hydrogen atom of the aryloxy is replaced with one selected from the same group of substituents as described in the case of substituted alkyl.

"Nonsubstituted heteroaryl" means univalent monocyclic organic compounds or bicyclic aromatic divalent organic compounds with 2-30 cyclic atoms that contains 1, 2 or 3 hetero atoms selected from the group consisting of N, O, P and S, and the remaining cyclic atoms therein is C, which is exemplified by thienyl, pyridyl, furyl, etc. "Substituted heteroaryl" indicates that at least one hydrogen atom of the nonsubstituted heteroaryl is replaced with one selected from the same group of substituents as described in the case of substituted alkyl.

"Nonsubstituted heteroarylalkyl" indicates that at least one hydrogen atom of the heteroaryl are replaced with a lower alkyl, and "substituted heteroarylalkyl" indicates that at least one hydrogen atom of the nonsubstituted heteroarylalkyl is replaced with one selected from the same group of substituents as described in the case of substituted alkyl.

"Nonsubstituted heteroaryloxy" indicates that an oxygen atom is bound to the heteroaryl. "Substituted heteroaryloxy" indicates that at least one hydrogen atom of nonsubstituted heteroaryloxy is replaced with one selected from the same group of substituents as described in the case of substituted alkyl.

"Nonsubstituted cycloalkyl" means univalent monocyclic organic compounds having 4-30 carbons, which are exemplified by cyclohexyl, cyclopentyl, etc. "Substituted cycloalkyl" indicates that at least one hydrogen atom of the nonsubstituted cycloalkyl is replaced with one selected from the same group of substituents as described in the case of substituted alkyl.

"Nonsubstituted heterocycloalkyl" means univalent monocyclic organic compounds having 1-30 cyclic atoms, which contain 1, 2, or 3 heteroatoms selected from the group consisting of N, O, P, or S, and the remaining cyclic atoms therein are C, and also indicates that at least one hydrogen atom is replaced with a lower alkyl. "Substituted heterocycloalkyl" indicates that at least one hydrogen atom of the nonsubstituted heterocycloalkyl is replaced with one selected from the same group of substituents as described in the case of substituted alkyl.

"Nonsubstituted alkylcarbonyl" is exemplified by acetyl, ethylcarbonyl, isopropylcarbonyl, phenylcarbonyl, naphthalenecarbonyl, diphenylcarbonyl, cyclohexylcarbonyl, etc. "Substituted alkylcarbonyl" indicates that at least one hydrogen atom of the nonsubstituted alkylcarbonyl is replaced with one selected from the same group of substituents as described in the case of substituted alkyl.

"Nonsubstituted arylcarbonyl" is exemplified by phenylcarbonyl, naphthalenecarbonyl, diphenylcarbonyl, etc. "Substituted arylcarbonyl" indicates that at least one hydrogen atom of the nonsubstituted arylcarbonyl is replaced with one selected from the same group of substituents as described in the case of substituted alkyl.

The organic metal compound of the present embodiments, represented by formula 1, shows excellent energy transfer resulting from the connecting structure of compounds for host and compounds for dopant having a different energy gap, respectively, and increased emission efficiency, as well as increased solubility owing to the increased molecular weight resulting from the connection.

The structure and a preparation method of an organic electroluminescence device using the organic metal compound of the present embodiments in which compounds for host and compounds for dopant are connected is described in detail below.

Figure 8:
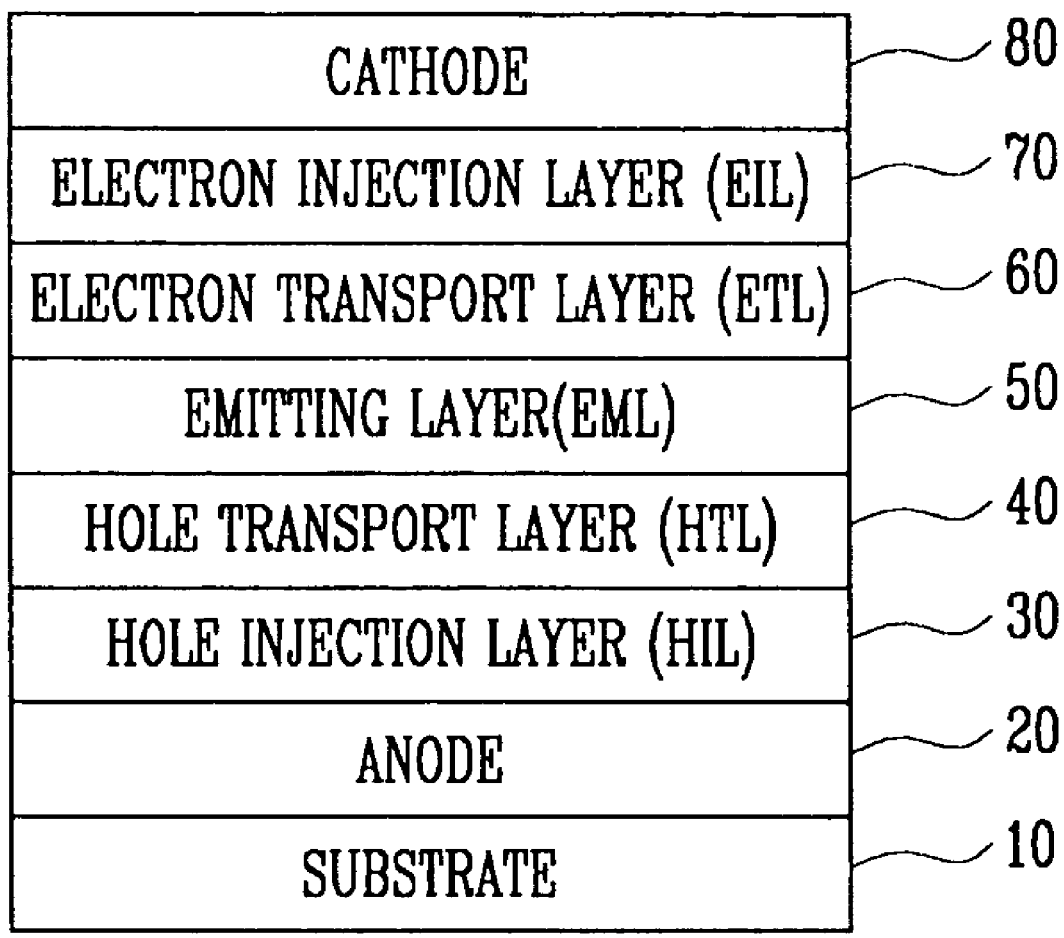
FIG. 8 shows the structure of the organic electroluminescence device of the present embodiments.

The organic electroluminescence device of the present embodiments can take the general form of a conventional organic electroluminescence device, or it can also be modified. Basically, the structure of an electroluminescence device contains an organic layer (emitting layer) between the first electrode (anode) and the second electrode (cathode), and can additionally include a hole injection layer, a hole transport layer, a hole blocking layer, an electron injection layer, or an electron transport layer. FIG. 8 shows the details of the structure of the organic electroluminescence device of the present embodiments.

As shown in FIG. 8, the organic electroluminescence device of the present embodiments accepts the structure having an emitting layer (50) between an anode (20) and a cathode (80), and in particular, additionally including a hole injection layer (30) and a hole transport layer (40) between the anode (20) and the emitting layer (50) and an electron transport layer (60) and an electron injection layer (70) between the emitting layer (50) and the cathode (80).

The electroluminescence device according one embodiment shown in FIG. 8 is prepared by the following processes.

First, the top of the substrate (10) is coated with materials for anode to form an anode (20). Herein, any generally accepted substrate can be used as the substrate, but particularly glass substrate or transparent plastic substrate is preferred owing to their excellent transparency and water-resistance, flatness of the surface, and ease in handling. As an anode electrode material generated on the substrate, indium tin oxide (ITO), tin oxide ($SnO_2$), and zinc oxide (ZnO), having great transparency and conductivity can be used.

The hole injection layer (HIL) (30) is selectively formed on the upper part of the anode (20). The hole injection layer is formed by conventional methods such as vacuum deposition or spin coating. Materials for the hole injection layer are not limited to specific ones but CuPc (copper phthalocyanine) or IDE 406 (Idemitsu Kosan Co.) can be used.

Then, the hole transport layer (HTL) (40) can be formed on the upper part of the hole injection layer (30) by vacuum deposition or spin coating. Materials for the hole transport layer are not limited to specific ones, but N,N'-bis(3-methylphenyl)-N,N'-diphenyl-[1,1-biphenyl]-4,4'-diamine (TPD), N,N'-di(naphthalene-1-yl)-N,N'-diphenylbenzidine, and N,N'-di(naphthalene-1-yl)-N,N'-diphenylbenzidine (a-NPD) are preferred.

Further, the emitting layer (EML) (50) is formed on the hole transport layer (40). As a material forming the emitting layer, the organic metal compound represented by formula 1 above in which compounds for host and compounds for dopant are connected can be adopted singly or together with other host materials such as CBP (4,4'-bis(carbazole-9-yl)-biphenyl).

The organic metal compound can be used to form the emitting layer using vacuum deposition as well as a wet process since the compound has a structure in which compounds for host are connected with compounds for dopant, increasing solubility with the increase of molecular weight. For example, spin coating, inkjet or laser thermal transfer methods can be used but the method is not limited thereto.

When the organic metal compound of the present embodiments in which compounds for host and compounds for dopant are connected is used, the level of doping is regulated by the number of molecules for host to be linked to compounds for dopant.

A hole blocking layer (HBL) may be selectively formed on top of the emitting layer (50) to prevent exitons from migrating to the electron transport layer or holes from migrating to the electron transport layer (60). The hole blocking layer forming materials are not limited to specific ones, but phenanthroline compounds (for example, BCP (2,9-dimethyl-4,7 diphenyl-1,10-phenanthroline)) are preferred. The hole blocking layer can be formed by vacuum deposition or spin coating.

The electron transport layer (ETL) (60) can be formed on the emitting layer (50), for which vacuum deposition or spin coating can also be used. The electron transport layer forming materials are not limited to specific ones, but an aluminum complex, for example Alq3(tris(8-quinolinolato)-aluminum), is preferred.

The electron injection layer (EIL) (70) can be formed on the electron transport layer (60) by vacuum deposition or spin coating. Electron injection layer forming materials are not limited to specific ones but LiF, NaCl, CsF, etc. are preferred.

The cathode (80) can be also formed on the electron injection layer (70) by vacuum deposition. Materials used for the formation of the cathode are exemplified by Li, Mg, Al, Al—Li, Ca, Mg—In, and Mg—Ag.

As shown in FIG. 8, the electroluminescence device of the present embodiments has a laminate structure, and if necessary, can additionally include one or two intermediate layers, such as hole blocking layer, etc. The thickness of each layer of the photoluminescence device can be determined in the generally acceptable range.

The present embodiments are described more precisely hereinafter, but the present embodiments are not limited to these specific examples.

Reagents

Products of Aldrich Co.: 2-bromopyridine, 2,4-difluorophenylboronic acid, 2-methoxy ethanol, 2-hydroxypicolinic acid, 18-crown-6, acetone, carbazole, 1,3-dibromo-5-methylbenzene, NBS, and AIBN Products of Across Co.: copper iodide; (+,−)-trans-1,2-diamino-cyclohexane; and -3,5-dihydroxybenzyl alcohol Products of Duksan Chemical Co.: magnesium sulfate; carbon tetrachloride; hexane; and diethyl ether Others: $Na_2CO_3$ and $K_2CO_3$ (Daejung), MeI (Sungyak Limited), tetrakis(triphenylphosphine)palladium (TCL), DME and 2-ethoxy ethanol (JUNSEI)

Confirmation of Compound

The structures of all the compounds newly synthesized were examined by $^1$H-NMR, $^{13}$C-NMR, UV and spectrofluorometer methods. The $^1$H-NMR and $^{13}$C-NMR spectra were obtained with a Bruker AM-300 spectrometer. A Beckman DU-650 for UV and JASCO FP-7500 were used for spectrofluorometry. All the chemical mobilities were recorded by the unit of ppm according to a solvent.

EXAMPLE 1

In the present embodiments, the compound of formula 7 is synthesized based on formula 2, in which M is Ir, and $R_1$-$R_5$ are H. The synthetic reaction scheme is as follows.

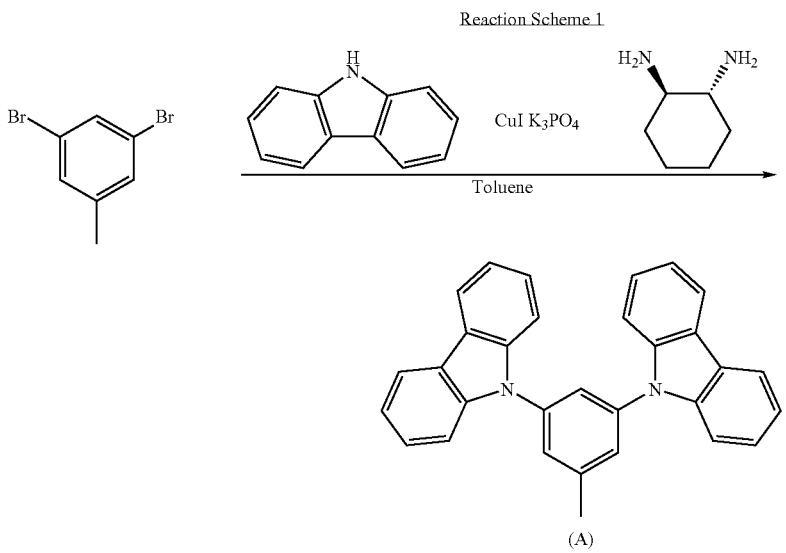

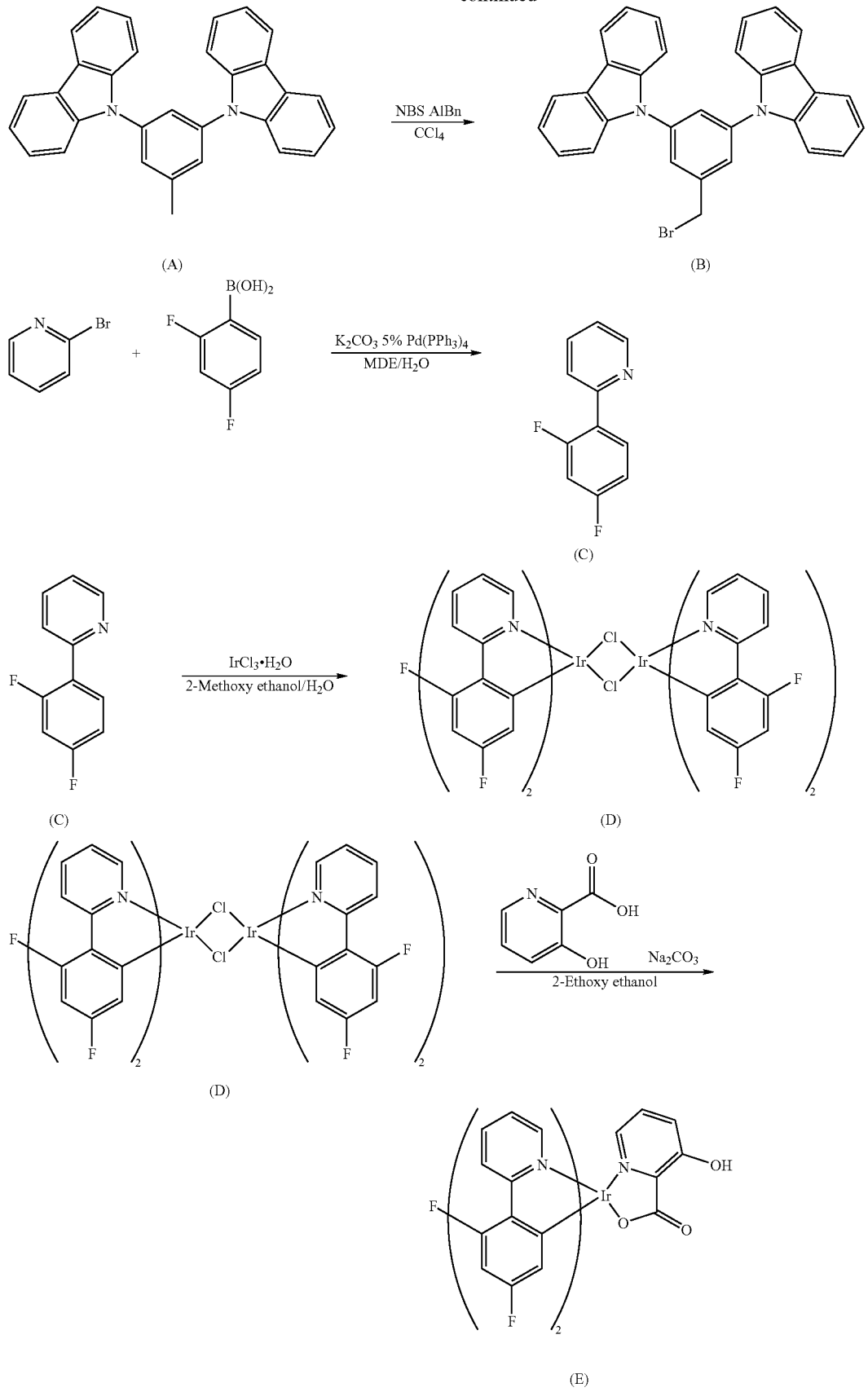

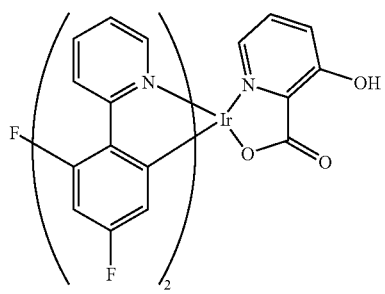

(E)

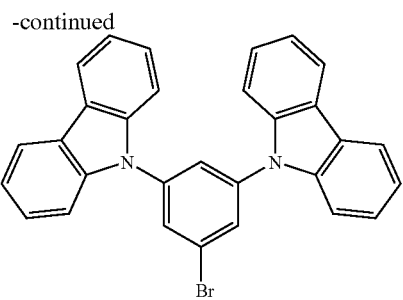

(B)

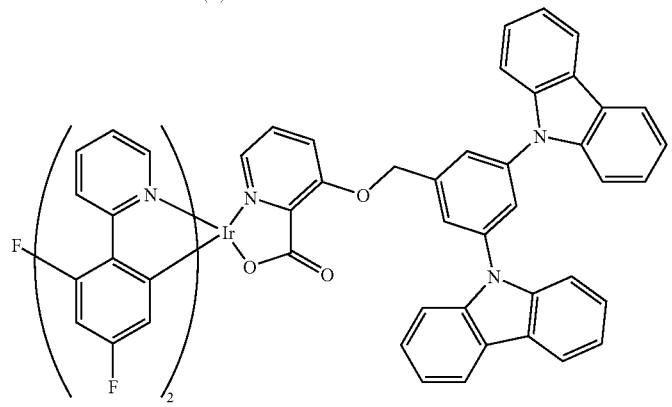

Formula 7

Synthesis of (A)

Copper iodide (0.01 mmol), potassium phosphate tribasic monohydrate (1.2 mmol), carbazole (1.2 mmol), and 1,4-dioxane (10 mL) were put in an airtight tube, to which nitrogen was injected, followed by stirring for 30 minutes. 1,3-dibromo-5-methylbenzene, (+,−)-trans-1,2-diaminocyclohexane (0.1 mmol) were added into the tube, which was then tightly sealed, followed by heat-stirring at 110° C. for 24 hours.

After confirming the reaction by TLC, the solvent was filtered by a glass filter and then removed by distillation under reduced pressure at high vacuum. Fresh column chromatography with methylene chloride was performed, resulting in a solid material. The product was dried for 3 hours by vacuum pump to give compound (A). The yield was 60%.

$^1$H-NMR (300 MHz, ((CD$_3$)$_2$CO)) spectrum results were as follows: d (ppm) 8.24 (d, J=3.8 Hz, 4H), 7.71 (s, 1H), 7.70-7.64 (m, 6H), 7.48 (t, J=7.7 Hz, 4H), 7.31 (t, J=8.5 Hz, 4H) 2.68 (s, 3H)

Synthesis of (B)

The compound (A) (0.1 mmol), NBS (01 mmol) and AIBN were put together in CCl$_4$ solvent, followed by heat-stirring at 80° C. for 12 hours. The reaction was confirmed by TLC, followed by filtering. The filtrate was washed with water and NaCl, and the solvent was removed under high vacuum. The residue was recrystallized from hexane and diethyl ether to give compound (B) as a brown solid. The yield was 40%.

$^1$H-NMR(CDCl$_3$, 300 MHz) spectrum results were as follows: d(ppm) 8.18 (d, J=3.8 Hz, 4H), 7.80 (s, 1H), 7.76 (s, 2H), 7.58 (d, J=4.2 Hz, 4H), 7.48 (t, J=8.2 Hz, 4H), 7.35 (t, J=7.7 Hz, 4H), 4.69 (s, 2H)

Synthesis of (C)

2-bromopyridine (1 mmol), 2,4-difluorophenylboronic acid (1.2 mmol), potassium carbonate (2.7 mmol), and dimethoxyethane (1.5 mL) were put together in a round bottom flask, to which nitrogen was injected, followed by stirring for 30 minutes. Tetrakis(triphenylphosphine)palladium (0.05 mmol) was added and a reflux condenser was connected thereto, followed by reflux at 90° C. for 18 hours. After confirming the reaction by TLC, the solvent was removed by distillation under reduced pressure at high vacuum. After extracting with ethyl acetate, the residue was purified by fresh column chromatography to give compound (C). The yield was 93%.

Synthesis of (D)

The compound (C) (10 mmol) was put in a round bottom flask, followed by 2-methoxy ethanol (13.1 mL), to which nitrogen was injected, followed by stirring for 30 minutes. IrCl$_3$·H$_2$O (4.5 mmol) was added and refluxed for 6 hours. Water was added to solidify and then the sample was filtered through a Buchner funnel, followed by drying in an infrared lamp to yield the compound (D) as a yellow solid. The yield was 70%.

Synthesis of (E)

3-hydroxypicolinic acid (3 mmol) and Na$_2$CO$_3$ were put together in a round bottom flask, followed by 2-ethoxy ethanol (100 ml), to which nitrogen was injected, and stirred for 30 minutes. The compound (D) (1 mmol) was then added and refluxed for 4 hours. The reaction was confirmed by TLC, and then the solvent was removed by distillation under reduced pressure at high vacuum. After removing the impurities through methylene chloride, the compound (E) was obtained as a fluorescent colored solid. The yield was 95%.

Synthesis of the Compound of Formula 7

The compound (E) (1 mmol) and the compound (B) (1 mmol) were put in a round bottom flask, followed by 18-crown-6 (1,4,7,10,13,16-hexaoxacyclootadecane) (0.1 mmol) and $K_2CO_3$ (1.2 mmol) and then acetone (30 mL) was added, followed by reflux for 7 hours.

After confirming the reaction by TLC, extracting with methylene chloride and separating with a column, the compound of formula 6 was obtained as a green solid. The yield was 43%.

$^1$H-NMR (($CD_3$)$_2$CO), 300 MHz) spectrum results were as follows: d (ppm) 8.701 (d, 5.4 Hz, 1H) 8.840 (d, 1.2 Hz, 1H) 8.318 (s, 1H) 8,246 (q, 6 Hz, 4H) 8.068 (t, 6 Hz, 3H) 7.937 (m, 3H) 7.785 (d, 6 Hz, 1H), 7.764 (s, 5.4 Hz, 5H) 7.575 (s, 1H), 7.432 (q, 8.1 Hz, 4H), 7.333 (q, 7.8 Hz, 4H) 7.123 (m, 1H), 6.579 (f, 9.3 Hz, 2H), 5.826 (q, 2.7 Hz, 1H), 5.569 (s, 2H), 5.553 (d, 8.8 Hz, 1H)

EXAMPLE 2

In the present embodiments, the compound of formula 11 is synthesized based on the compound of formula 3, in which M is Ir, $R_1$-$R_5$ are H, and $R_7$ is alkoxy with 12 carbon atoms. The synthetic reaction scheme is as follows.

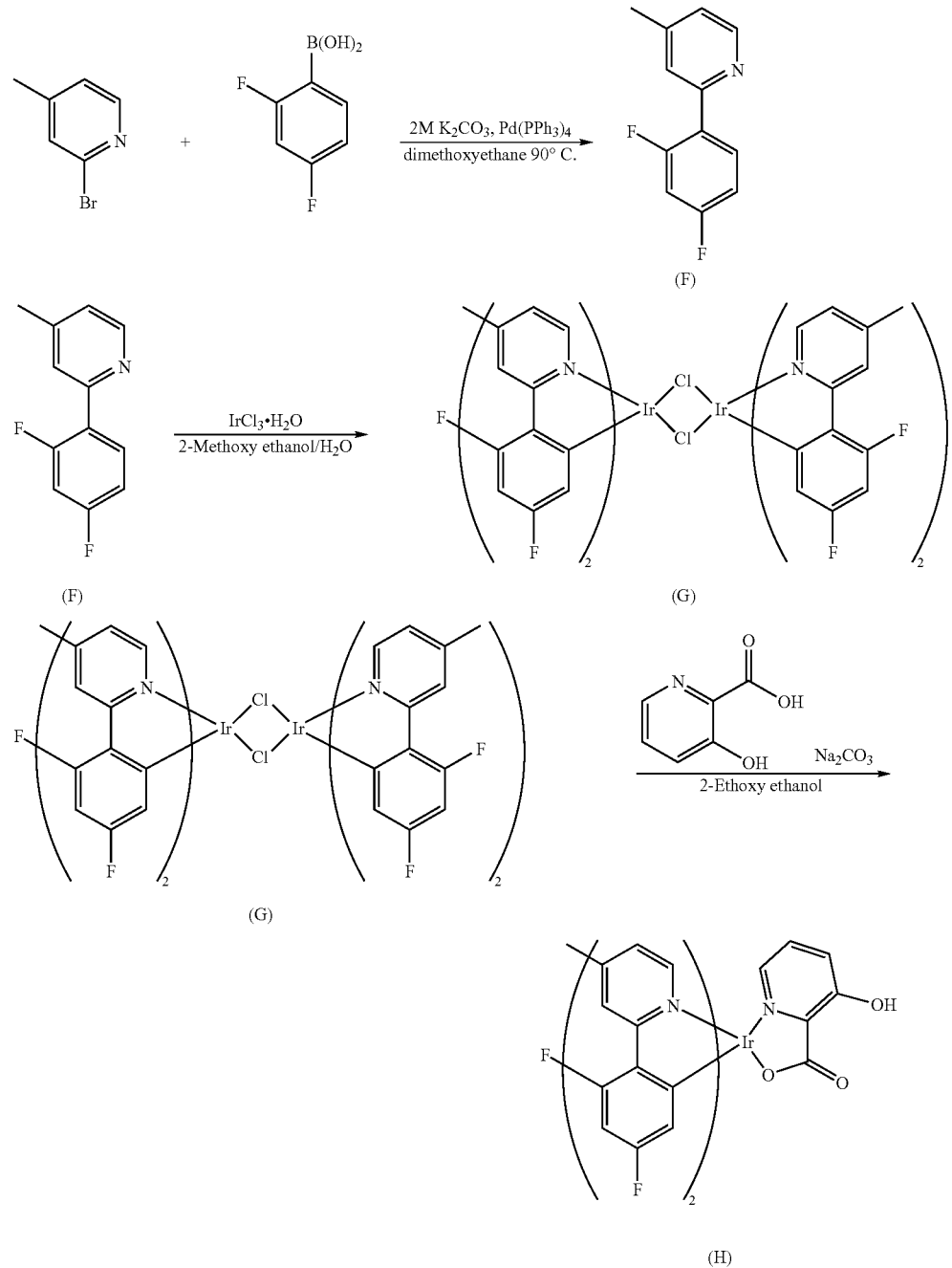

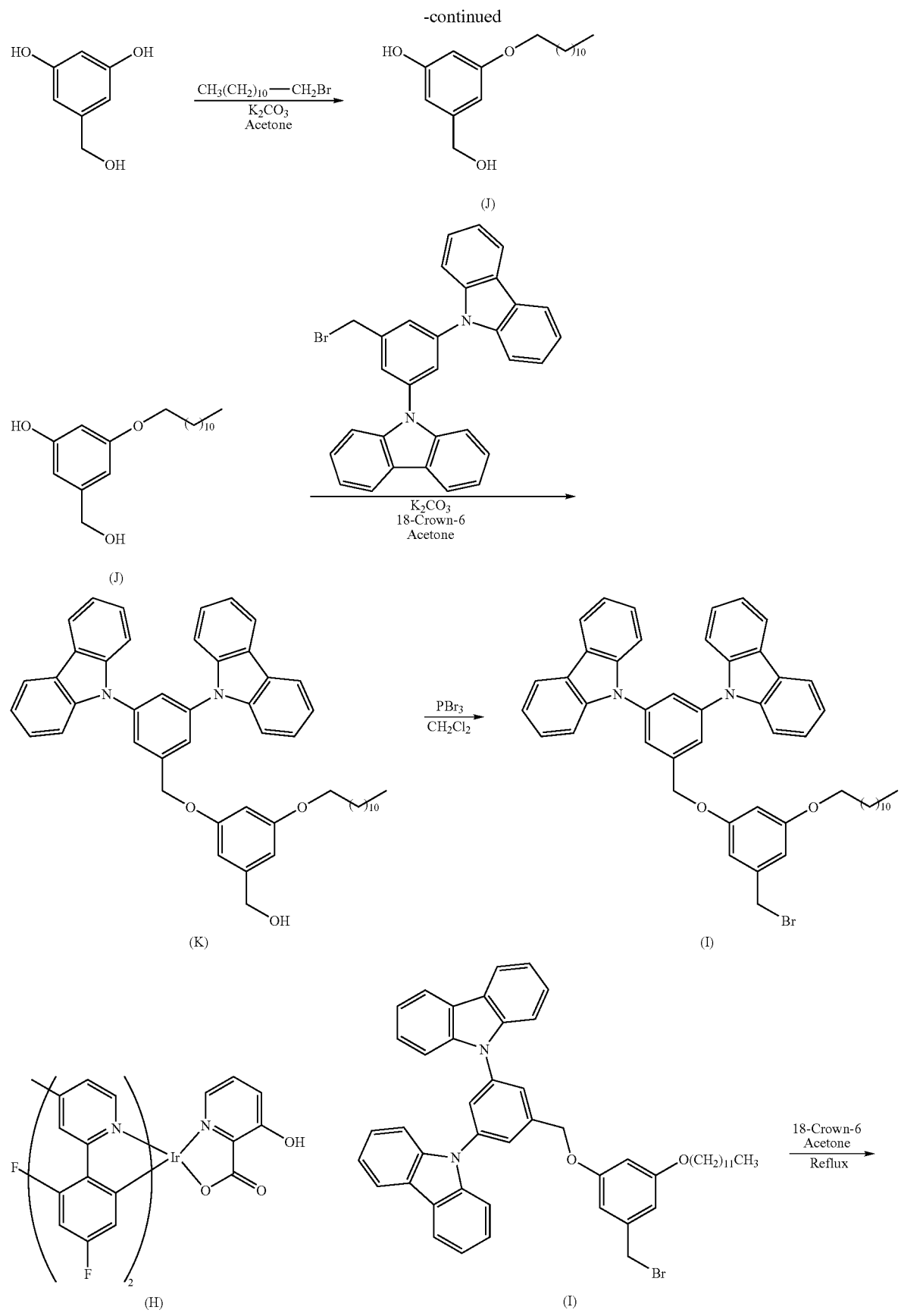

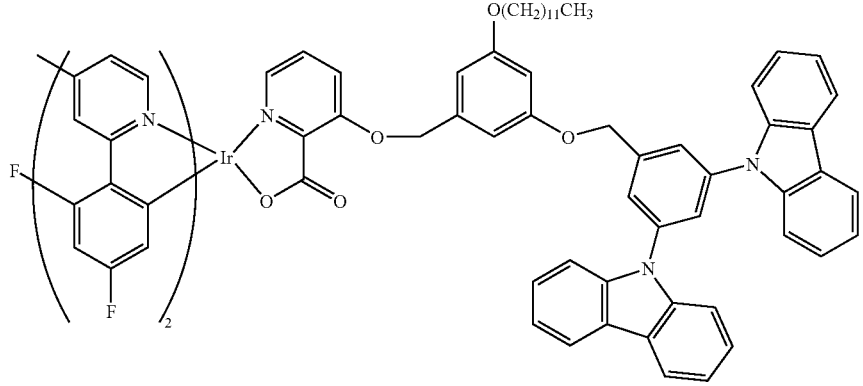

Formula 11

Synthesis of (F)

2-bromo-4-methylpyridine (1 mmol), 2,4-difluorophenylboronic acid (1.2 mmol), potassium carbonate (2.7 mmol), and dimethoxyethane (1.5 mL) were put together in a round bottom flask, to which nitrogen was injected, followed by stirring for 30 minutes. Tetrakis(triphenylphosphine)palladium (0.05 mmol) was added and a reflux condenser was connected thereto, followed by reflux at 90° C. for 18 hours. After confirming the reaction by TLC, the solvent was removed by distillation under reduced pressure at high vacuum. After extracting with ethyl acetate, the residue was purified by fresh column chromotography to give a liquid material, the compound (F). The yield was 93%.

$^1$H-NMR(300 MHz, CDCl$_3$) spectrum results were as follows: d(ppm) 8.59 (d, J=3.0 Hz, 1H), 7.99 (dd, J=6, 1.5 Hz, 1H), 7.60 (s, 1H), 7.13 (d, J=3 Hz, 1H), 7.03 (d, J=3.9 Hz, 1H), 6.97-6.90(m, 2H), 2.45 (s, 3H)

Synthesis of (G)

The compound (F) (10 mmol) was put in a round bottom flask, followed by 2-methoxy ethanol (13.1 mL), to which nitrogen was injected, followed by stirring for 30 minutes. IrCl$_3$·H$_2$O (4.5 mmol) was added and the solution was refluxed for 6 hours. Water was added to solidify and then the sample was filtered through a Buchner funnel, followed by drying in an infrared lamp to yield the compound (G) as a yellow solid. The yield was 70%.

Synthesis of (H)

3-hydroxypicolinic acid (3 mmol) and Na$_2$CO$_3$ were put together in a round bottom flask, followed by 2-ethoxy ethanol (100 ml), to which nitrogen was injected, and stirred for 30 minutes. The compound (G) (1 mmol) was then added and refluxed for 4 hours. The reaction was confirmed by TLC, and then the solvent was removed by distillation under reduced pressure at high vacuum. After removing the impurities through methylene chloride, the compound (H) was obtained as a-fluorescent colored solid. The yield was 95%.

Synthesis of (J)

3,5-dihydroxybenzyl alcohol (10 mmol), dodecyl bromide (10 mmol) and K$_2$CO$_3$ (10 mmol) were put in a round bottom flask, followed by acetone (200 mL) and then refluxed for 12 hours. The reaction was confirmed by TLC, and then the inorganic materials were removed through a glass filter and washed with methylene chloride. After removing the solvent and separating through a column, the compound (J) was obtained. The yield was 50%.

Synthesis of (K)

The compound (J) (1 mmol) and the compound (B) (1 mmol) were put in a round bottom flask, followed by 18-crown-6 (0.1 mmol), K$_2$CO$_3$ (1.2 mmol) and acetone (30 mL) and then refluxed for 7 hours. The reaction was confirmed by TLC, and then the solvent was removed and purified through a column to give the compound (K) as a viscous liquid. The yield was 72%.

Synthesis of (I)

The compound (K) (1 mmol) and PBr$_3$ (1.5 mmol) were put in a solvent, followed by stirring for 2 hours at 0° C. After confirmation by TLC and separating through a column, the compound (I) was obtained. The yield was 68%.

$^1$H-NMR (CDCl$_3$, 300 MHz) spectrum results were as follows: d(ppm) 8.18(d, J=3.9 Hz, 4H), 7.81-7.79(br m, 3H), 7.54(d, J=4.1 Hz, 4H), 7.54 (t, J=8.2 Hz, 4H), 7.54(t, J=8.2 Hz, 4H), 7.34(t, J=7.92 Hz, 4H), 6.67(s, 1H), 6.63(s, 1H), 6.54 (s, 1H), 5.32(s, 2H), 4.46(s, 2H), 3.95(t, J=6.5 Hz, 2H), 1.83-1.74(m, 4H), 1.45 1.40(br, s, 2H), 1.28(s, 16H), 0.91(t, J=10.3 Hz, 2H).

Synthesis of the Compound of Formula 11

The compound (H) (0.5 mmol) and the compound (I) (0.5 mmol) were put in a round bottom flask, followed by 18-crown-6 (0.05 mmol) and K$_2$CO$_3$ (0.6 mmol) and then acetone (20 mL), followed by reflux for 7 hours. After confirming the reaction by TLC and then separating through a column, the compound of formula 11 was obtained. The yield was 50%.

$^1$H-NMR ((CD$_3$)$_2$CO, 300 MHz) spectrum results were as follows: d(ppm) 8.53(d, J=3.0 Hz, 1H),) 8.25 (d, J=3.5 Hz, 4H), 8.11(s, 2H), 7.89 7.32(m, 3H), 7.82(d, J=1.9 Hz, 1H), 7.6(d, J=4.1 Hz, 4H), 7.54(d, J=3.0 Hz, 1H), 7.48(d, J=3.0 Hz, 2H), 7.40(t, J=8.3 Hz, 5H), 7.26(t, J=7.9 Hz, 4H), 7.17(d, J=2.5 Hz, 1H), 6.98 8.96(m, 2H), 6.60 6.49(m, 3H), 5.83(dd, J=1.2 Hz, 4.4 Hz, 1H), 5.60(s, 3H), 5.32(s, 2H), 3.99(t, J=5.7 Hz, 2H), 2.57(s, 3H), 2.52 (s, 3H), 1.85(t, J=2.3 Hz, 2H), 1.38(br s, 2H), 1.25(s, 16H), 0.86(t, J=6.7 Hz, 3H)

EXAMPLE 3

In the present embodiments, the compound of formula 10 based on formula 3, in which M is Ir, R$_1$-R$_5$ are H, and R$_7$ is alkoxy with 12 carbon atoms is synthesized. The synthetic reaction scheme is as follows.

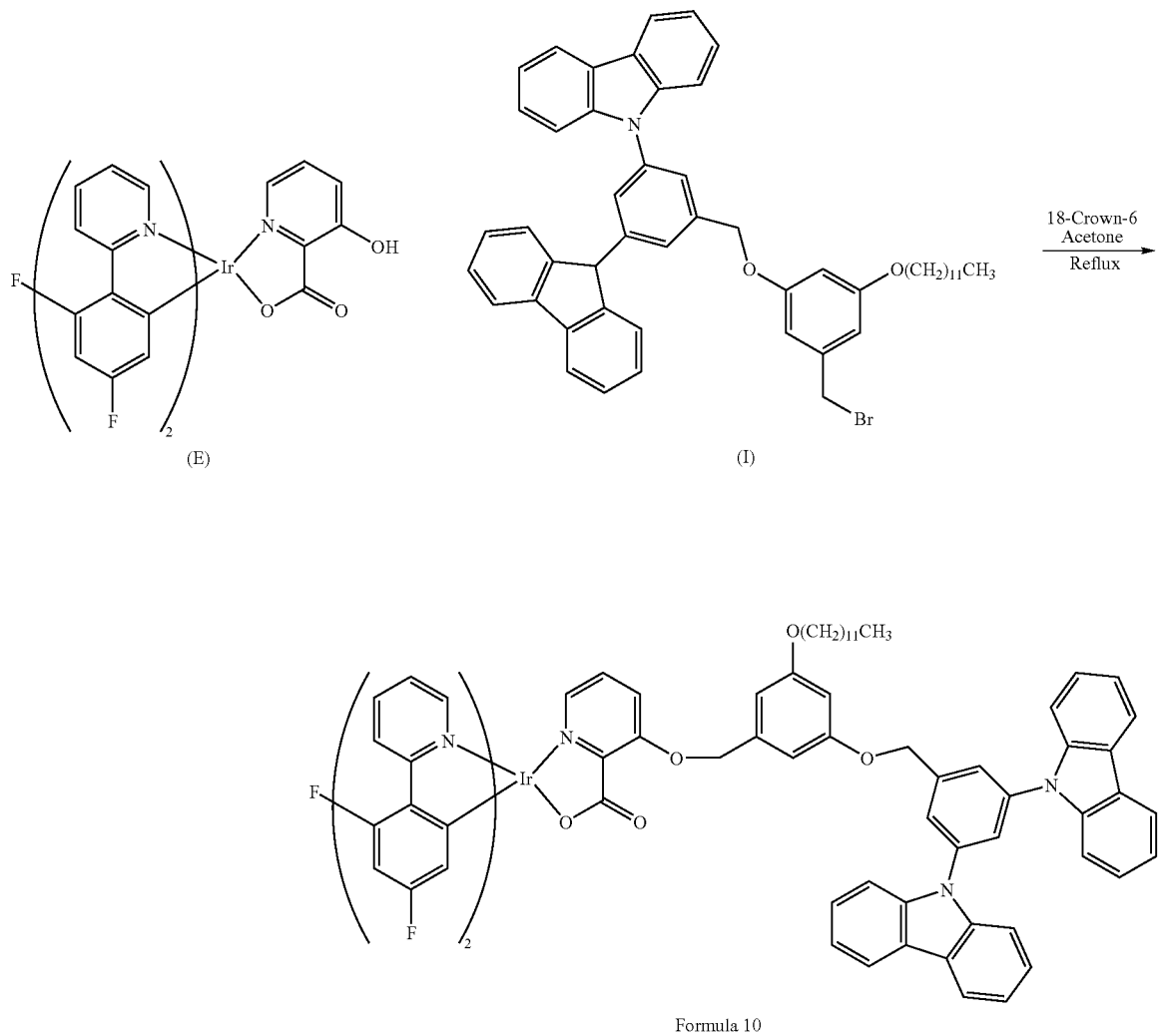

Reaction Scheme 3

Synthesis of the Compound of Formula 10

The compound (E) (0.5 mmol) obtained in Example 1 and the compound (I) (0.5 mmol) obtained in Example 2 were put in a round bottom flask, followed by 18-crown-6 (0.05 mmol) and $K_2CO_3$ (0.6 mmol) and then acetone (20 mL), followed by reflux for 7 hours. After confirming the reaction by TLC and separating through a column, the compound of formula 10 was obtained. The yield was 50%.

$^1$H-NMR ($(CD_3)_2CO$, 300 MHz) spectrum results were as follows: d(ppm) 8.74(d, J=2.8 Hz, 1H), 8.30(t, J=6.7 Hz, 2H), 8.22(d, J=3.9 Hz, 4H), 7.98(q, J=3.9 Hz, 2H), 7.90 7.84(m, 4H), 7.78(d, J=4.1 Hz, 1H), 7.64(d, J=4.1 Hz, 4H), 7.51 7.49(m, 2H), 7.51 7.49(m, 2H), 7.44 7.34(m, 6H), 7.27(t, J=7.5 Hz, 4H), 7.21(t, J=5.9 Hz, 1H), 6.97(s, 1H), 6.66 6.53 (m, 3H), 5.82(dd, J=1.2 Hz, 4.4 Hz, 1H), 5.61(s, 3H), 5.40(s, 2H), 3.99(t, J=6.1 Hz, 2H), 1.85(t, J=2.2 Hz, 2H), 1.35(br s, 2H), 1.25(s, 16H), 0.86(t, J=6.7 Hz, 3H).

COMPARATIVE EXAMPLE 1

Synthesis of the Compound of Formula 16

Reaction Scheme 4

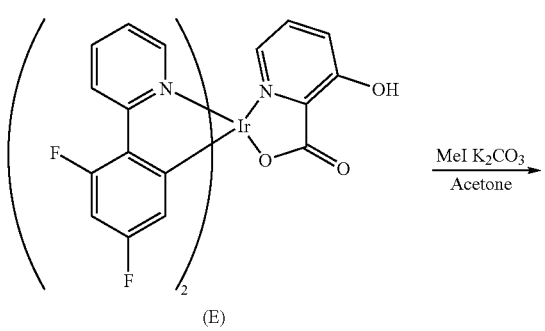

-continued

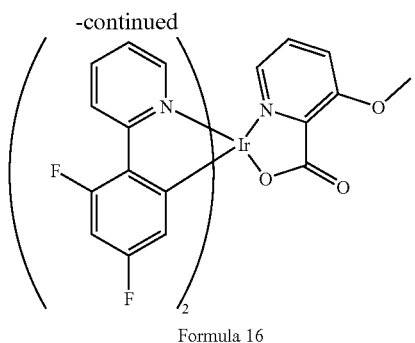

Formula 16

The compound (E) (1 mmol), MeI (3 mmol) and K₂CO₃ (2 mmol) were put in a round bottom flask, followed by acetone (30 mL) and refluxed for 5 hours. After confirming the reaction by TLC, extracting with methylene chloride and separating through a column, the compound of formula 16 was obtained as a lemon-colored solid. The yield was 50%.

$^1$H-NMR(CD$_3$)$_2$CO, 300 MHz) spectrum results were as follows: d(ppm) 8.773(d, 4.8 Hz, 1H), 8.335(t, 9.3 Hz, 2H), 8.049(t, 4.8 Hz, 2H), 7.511(m, 1.2 Hz, 3H), 7.295(t, 7.2 Hz, 1H), 6.548(m, 2.4 Hz, 2H), 5.840(q, 8.7 Hz, 1H), 5.590(q, 8.7 Hz, 1H)

The photoluminescence properties of the compounds of formulae 7 and 11, synthesized in Examples 1 and 2, were investigated. The photoluminescence properties of compounds of formula 16, synthesized in Comparative Examples 1, were also investigated for the comparison.

Figure 2:
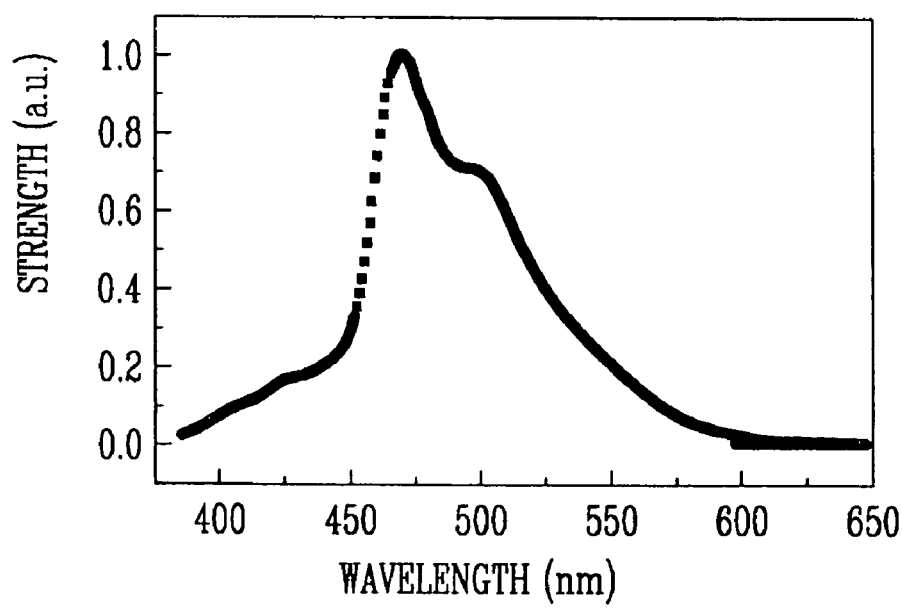
FIG. 2 is a graph showing a PL spectrum in THF solution of the compound represented by formula 16, synthesized in Comparative Example 1.
Figure 3:
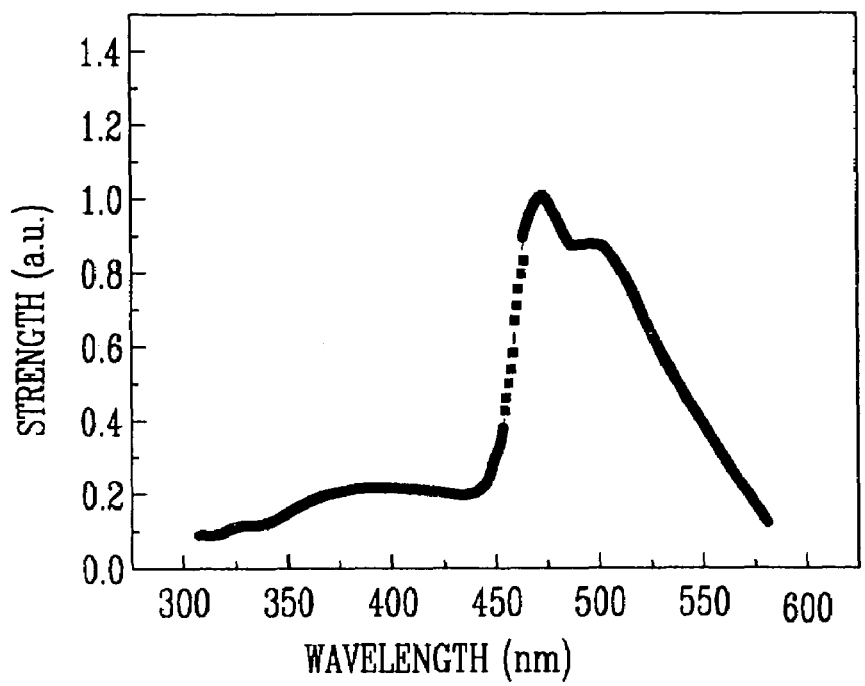
FIG. 3 is a graph showing PL spectra when 20% doped in a PMMA polymer film of the compound represented by formula 7, synthesized in Example 1.
Figure 4:
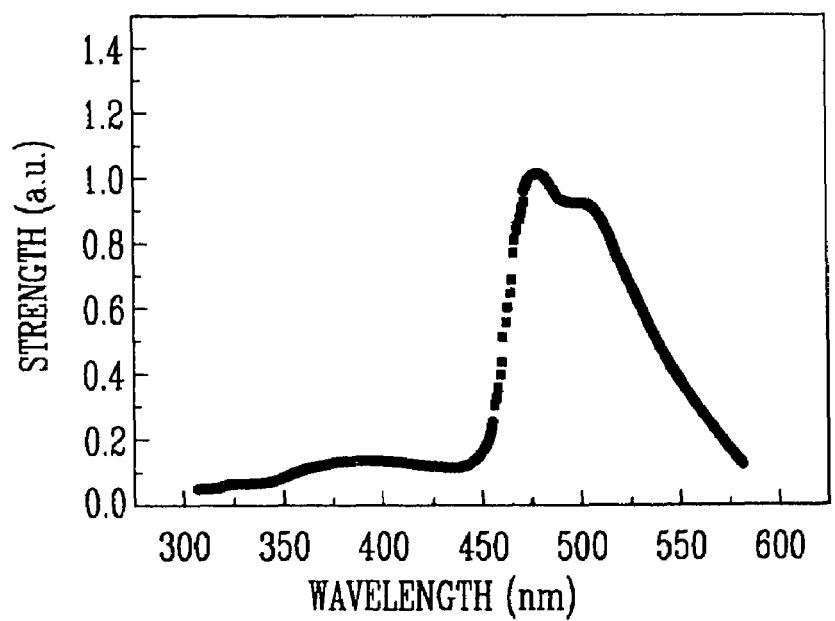
FIG. 4 is a graph showing PL spectra when 20% doped in a PMMA polymer film of the compound represented by formula 11, synthesized in Example 2.

FIG. 1 shows the photoluminescence (PL) spectrum in THF solution of the compound of formula 7 synthesized in Example 1. FIG. 2 shows the photoluminescence spectrum in THF solution of the compound of formula 16 synthesized in Comparative Example 1. FIG. 3 shows the comparison of PL spectra when doped in a PMMA high molecular film at 20% of the compound represented by formula 7, synthesized in Example 1. FIG. 4 shows the comparison of PL spectra when 20% doped in a PMMA polymer film of the compound represented by formula 11, synthesized in Example 2. FIG. 5 shows the comparison of PL spectra in chloroform solution between the compound synthesized in Example 1 and the compound synthesized in Comparative Example 1.

As shown in FIGS. 1 and 2, the compound of formula 7 showed a blue emitting in 470 nm, while the compound of formula 16 showed a blue emitting in 475 nm. As shown in FIGS. 3 and 4, the compounds of formulae 7 and 11 showed a blue emitting in 472 nm and 479 nm, respectively. In addition, as shown in FIG. 5, photoluminescence property of the organic metal compound of Example 1, in which compounds for host and compounds for dopant were connected, was much greater than that for those using the compound of formula 16 only for a dopant.

Figure 6A:
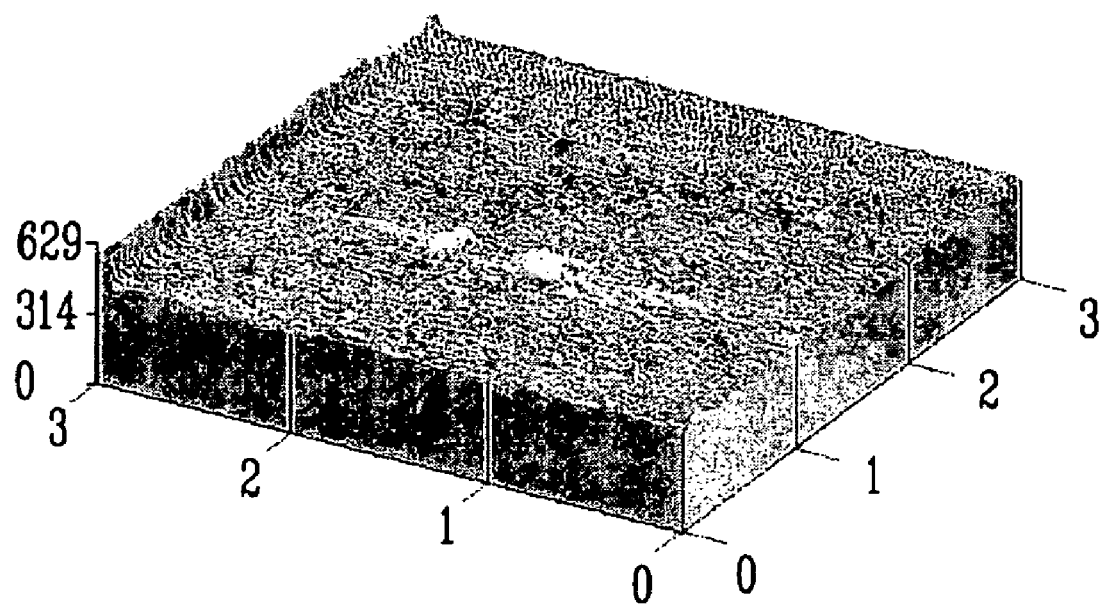
FIGS. 6A and 6B show an AFM-morphology image of the layer obtained by dissolving the compound of formula 7 synthesized in Example 1 in solvent followed by spin coating.
Figure 6B:
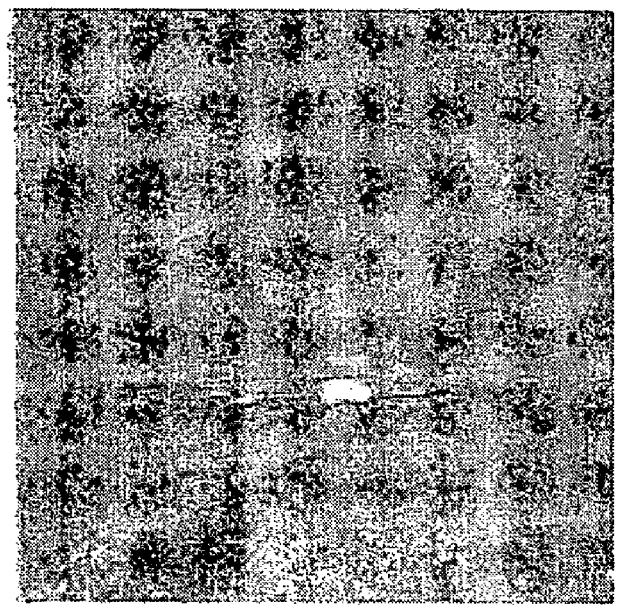
Figure 7A:
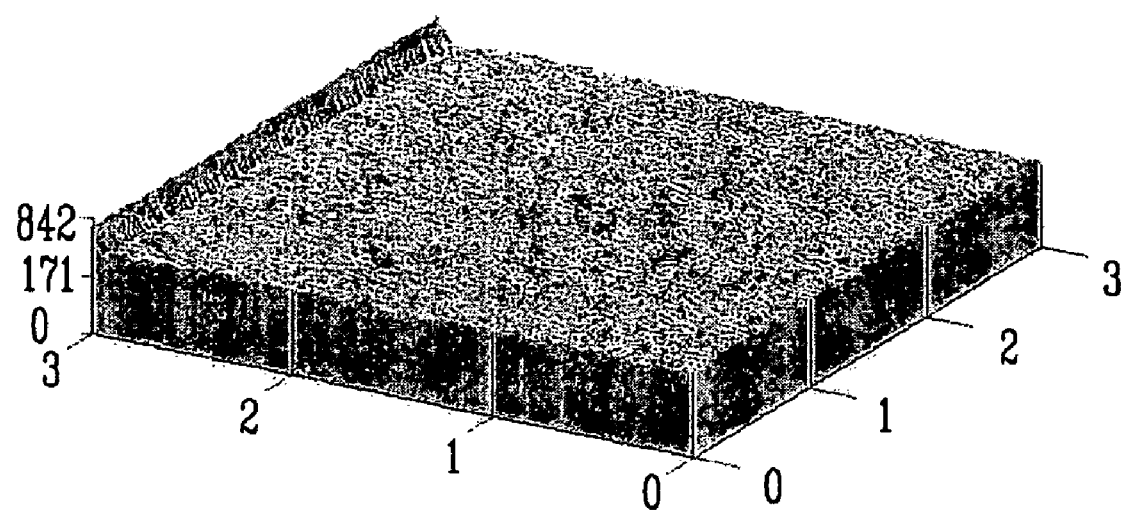
FIGS. 7A and 7B show an AFM-morphology image of the layer obtained by dissolving the compound of formula 11 synthesized in Example 2 in solvent followed by spin coating.
Figure 7B:
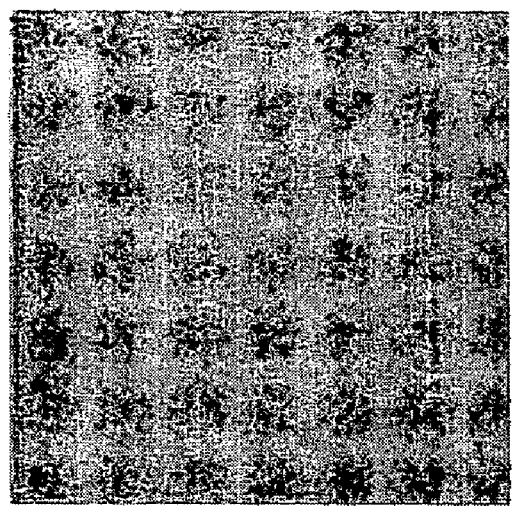

In addition, FIGS. 6 and 7 show an AFM-morphology image of the layer obtained by dissolving the compounds of formulae 7 and 11 synthesized in Examples 1 and 2 in each solvent followed by spin coating.

EXAMPLE 4

For an anode, a 10 Ω/cm² substrate provided by Coming Co. was used, and on top of the substrate, IDE 406(Idemitsu Kosan Co.) was vacuum-deposited to form a 600 Å thick hole injection layer. Next, on top of the hole injection layer, N,N'-diphenyl-N,N'-bis(3-methylphenyl)-1,1'-biphenyl-4,4'-diamine(TPD) compound was vacuum-deposited to form a 300 Å thick hole transport layer. Upon completion of the formation of the hole transport layer, a 200 Å thick emitting layer was formed by 12% doping of the compound of formula 7 to CBP, on the top of the hole transport layer. Then, on top of the emitting layer, BCP was vacuum-deposited to form a 50 Å thick hole blocking layer. And on the upper part of the hole blocking layer, Alq3 was vacuum-deposited to form a 200 Å thick electron transport layer. On top of the electron transport layer, LiF (10 Å thick) and Al(aluminum) (3000 Å thick) were serially vacuum-deposited, resulting in the generation of a LiF/Al electrode. As a result, an organic electroluminescence device was prepared.

Efficiency, driving voltage, color purity and lifetime of the organic electroluminescence device prepared in Example 4 were investigated which proved to have excellent efficiency, driving voltage, color purity, and lifetime.

The effects of the present embodiments are as follows.

First, the organic metal compounds of the present embodiments can be effectively used as a coloring material of a photoluminescence device since the have low moleculard level emitting properties.

Second, the organic metal compounds of the present embodiments have structures having the connection of the compounds for host and the compounds for dopant, so that their stability can be remarkably increased owing to the increased molecular weight (even though each compound has low molecular weight, when they are connected with each other to form a compound, the resultant compound has a high molecular weight). Thus, a wet process such as spin coating can be applied for the preparation of an electroluminescence or photoluminescence device.

Third, the photoluminescence device prepared by using the organic metal compound of the present embodiments has enhanced EL properties such as efficiency, brightness, driving voltage, and the like.

Although a few embodiments of the present embodiments have been shown and described, it would be appreciated by those skilled in the art that changes may be made in these embodiments without departing from the principles and spirit of the embodiments, the scope of which is defined below in the claims and their equivalents.

What is claimed is:

1. An organic metal compound represented by the following formula 1 in which compounds for host and compounds for dopant are connected:

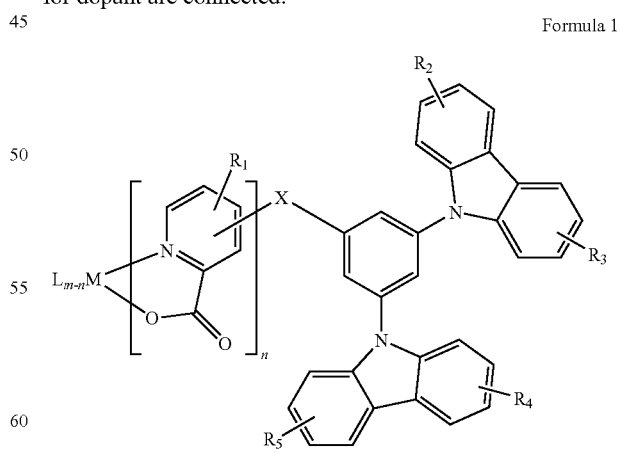

Formula 1 wherein, X is selected from the following structures;
X1:

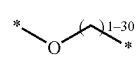

-continued

X2:

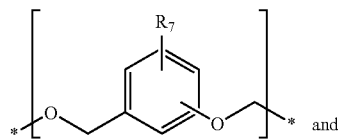
and

X3:

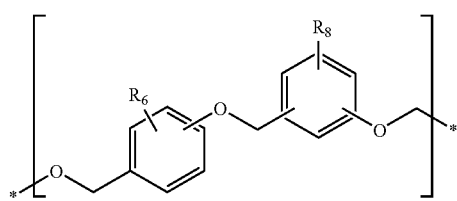

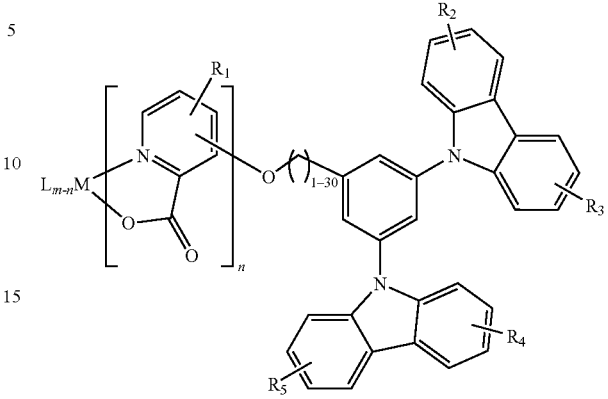

Formula 2

$R_1$-$R_8$ are each independently selected from mono-substituted or multi-substituted functional groups selected from the group consisting of H, cyano, hydroxy, thiol, halogen atoms, substituted or nonsubstituted $C_1$-$C_{30}$ alkyl, substituted and nonsubstituted $C_1$-$C_{30}$ alkoxy, substituted and nonsubstituted $C_2$-$C_{30}$ alkenyl, substituted and nonsubstituted $C_6$-$C_{30}$ aryl, substituted and nonsubstituted $C_6$-$C_{30}$ arylalkyl, substituted and nonsubstituted $C_6$-$C_{30}$ aryloxy, substituted or nonsubstituted $C_2$-$C_{30}$ heteroaryl, substituted and nonsubstituted $C_2$-$C_{30}$ heteroarylalkyl, substituted and nonsubstituted $C_2$-$C_{30}$ heteroaryloxy, substituted and nonsubstituted $C_5$-$C_{30}$ cycloalkyl, substituted and nonsubstituted $C_2$-$C_{30}$ heterocycloalkyl, substituted and nonsubstituted $C_1$-$C_{30}$ alkylcarbonyl, substituted and nonsubstituted $C_7$-$C_{30}$ arylcarbonyl, $C_1$-$C_{30}$ alkylthiol, —Si(R')(R")(R''') wherein, R', R" and R''' are independently H or $C_1$-$C_{30}$ alkyl, and —N(R')(R") wherein R' and R" are independently H or $C_1$-$C_{30}$ alkyl, and the neighboring groups among functional groups of $R_1$-$R_8$ can be linked to each other to form a ring;

wherein M is selected from the group consisting of Ir, Os, Pt, Pb, Re and Ru;

and wherein L is bidentate ligand, m is 3, and n is 1 or 2.

2. The organic metal compound of claim 1, represented by Formula 2:

wherein, $R_1$-$R_5$ are each independently selected from mono-substituted or multi-substituted functional groups selected from the group consisting of H, cyano, hydroxy, thiol, halogen atoms, substituted or nonsubstituted $C_1$-$C_{30}$ alkyl, substituted and nonsubstituted $C_1$-$C_{30}$ alkoxy, substituted and nonsubstituted $C_2$-$C_{30}$ alkenyl, substituted and nonsubstituted $C_6$-$C_{30}$ aryl, substituted and nonsubstituted $C_6$-$C_{30}$ arylalkyl, substituted and nonsubstituted $C_6$-$C_{30}$ aryloxy, substituted or nonsubstituted $C_2$-$C_{30}$ heteroaryl, substituted and nonsubstituted $C_2$-$C_{30}$ heteroarylalkyl, substituted and nonsubstituted $C_2$-$C_{30}$ heteroaryloxy, substituted and nonsubstituted $C_5$-$C_{30}$ cycloalkyl, substituted and nonsubstituted $C_2$-$C_{30}$ heterocycloalkyl, substituted and nonsubstituted $C_1$-$C_{30}$ alkylcarbonyl, substituted and nonsubstituted $C_7$-$C_{30}$ arylcarbonyl, $C_1$-$C_{30}$ alkylthiol, —Si(R')(R")(R''') wherein, R', R" and R''' are independently H or $C_1$-$C_{30}$ alkyl, and —N(R')(R") wherein R' and R" are independently H or $C_1$-$C_{30}$ alkyl, and the neighboring groups among functional groups of $R_1$-$R_5$ can be linked to each other to form a ring;

wherein M is selected from the group consisting of Ir, Os, Pt, Pb, Re and Ru;

and wherein L is bidentate ligand, m is 3, and n is 1 or 2.

3. An organic metal compound represented by the following Formula 3:

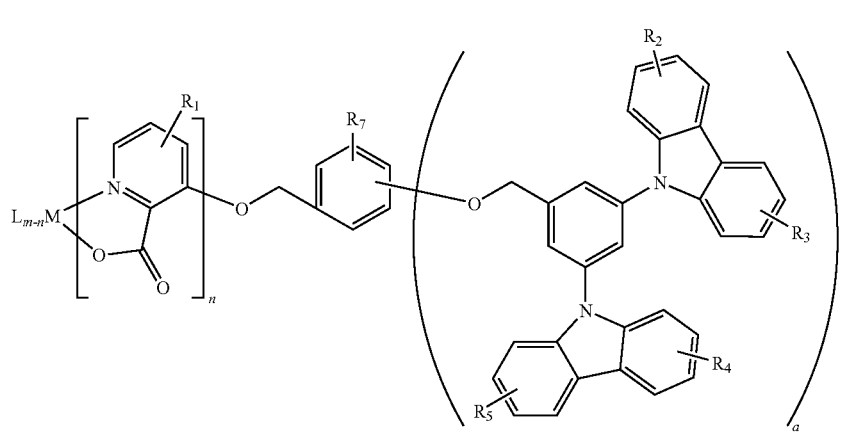

Formula 3 wherein, $R_1$-$R_5$, and $R_7$ are each independently selected from mono-substituted or multi-substituted functional groups selected from the group consisting of H, cyano, hydroxy, thiol, halogen atoms, substituted or nonsubstituted $C_1$-$C_{30}$ alkyl, substituted and nonsubstituted $C_1$-$C_{30}$ alkoxy, substituted and nonsubstituted $C_2$-$C_{30}$ alkenyl, substituted and nonsubstituted $C_6$-$C_{30}$ aryl, substituted and nonsubstituted $C_6$-$C_{30}$ arylalkyl, substituted and nonsubstituted $C_6$-$C_{30}$ aryloxy, substituted or nonsubstituted $C_2$-$C_{30}$ heteroaryl, substituted and nonsubstituted $C_2$-$C_{30}$ heteroarylalkyl, substituted and nonsubstituted $C_2$-$C_{30}$ heteroaryloxy, substituted and nonsubstituted $C_5$-$C_{30}$ cycloalkyl, substituted and nonsubstituted $C_2$-$C_{30}$ heterocycloalkyl, substituted and nonsubstituted $C_1$-$C_{30}$ alkylcarbonyl, substituted and nonsubstituted $C_7$-$C_{30}$ arylcarbonyl, $C_1$-$C_{30}$ alkylthiol, —Si(R')(R")(R'") wherein, R', R" and R'" are independently H or $C_1$-$C_{30}$ alkyl, and —N(R')(R") wherein R' and R" are independently H or $C_1$-$C_{30}$ alkyl, and the neighboring groups among functional groups of $R_1$-$R_5$ and $R_7$ can be linked to each other to form a ring;

wherein M is selected from the group consisting of Ir, Os, Pt, Pb, Re and Ru;

and wherein L is bidentate ligand, m is 3, and n is 1 or 2 and a is 1, 2 or 3.

4. An organic metal compound represented by the following Formula 4:

and R" are independently H or $C_1$-$C_{30}$ alkyl, and the neighboring groups among functional groups of $R_1$-$R_5$, $R_6$ and $R_8$ can be linked to each other to form a ring;

wherein M is selected from the group consisting of Ir, Os, Pt, Pb, Re and Ru;

and wherein L is bidentate ligand, m is 3, and n is 1 or 2; and a is 1, 2 or 3.

5. The organic metal compound as set forth in claim 1, wherein L has any one of the following structures:

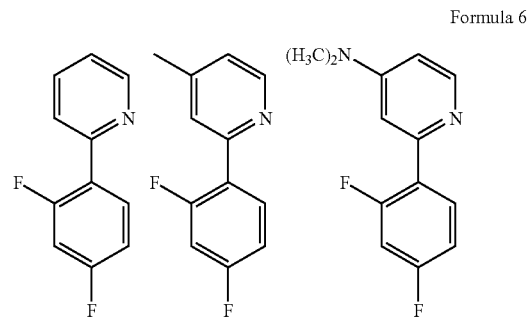

Formula 6

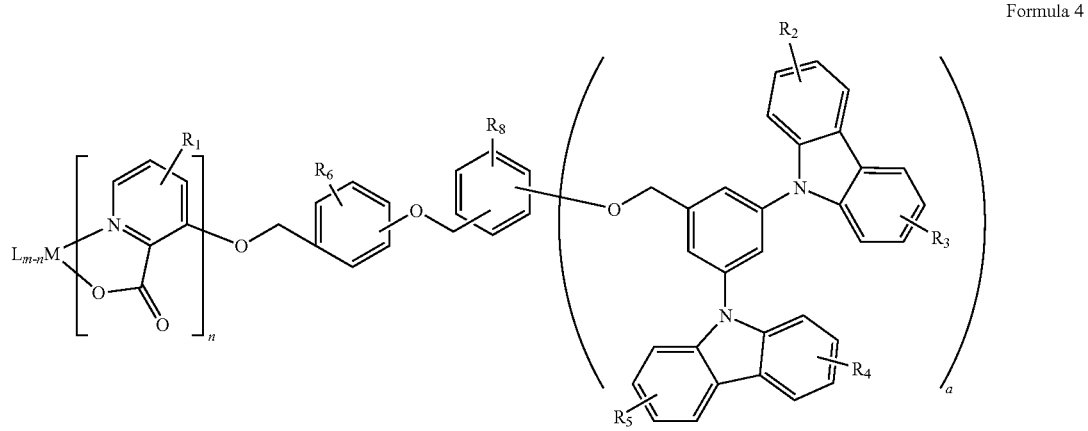

Formula 4 wherein, $R_1$-$R_5$, $R_6$ and $R_8$ are each independently selected from mono-substituted or multi-substituted functional groups selected from the group consisting of H, cyano, hydroxy, thiol, halogen atoms, substituted or nonsubstituted $C_1$-$C_{30}$ alkyl, substituted and nonsubstituted $C_1$-$C_{30}$ alkoxy, substituted and nonsubstituted $C_2$-$C_{30}$ alkenyl, substituted and nonsubstituted $C_6$-$C_{30}$ aryl, substituted and nonsubstituted $C_6$-$C_{30}$ arylalkyl, substituted and nonsubstituted $C_6$-$C_{30}$ aryloxy, substituted or nonsubstituted $C_2$-$C_{30}$ heteroaryl, substituted and nonsubstituted $C_2$-$C_{30}$ heteroarylalkyl, substituted and nonsubstituted $C_2$-$C_{30}$ heteroaryloxy, substituted and nonsubstituted $C_5$-$C_{30}$ cycloalkyl, substituted and nonsubstituted $C_2$-$C_{30}$ heterocycloalkyl, substituted and nonsubstituted $C_1$-$C_{30}$ alkylcarbonyl, substituted and nonsubstituted $C_7$-$C_{30}$ arylcarbonyl, $C_1$-$C_{30}$ alkylthiol, —Si(R')(R")(R'") wherein, R', R" and R'" are independently H or $C_1$-$C_{30}$ alkyl, and —N(R')(R") wherein R'

-continued

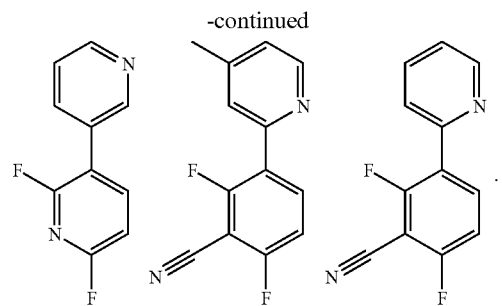

6. An organic metal compound, wherein the structure of the compound is selected from the group consisting of the compounds having formulae 7-15:

Formula 7
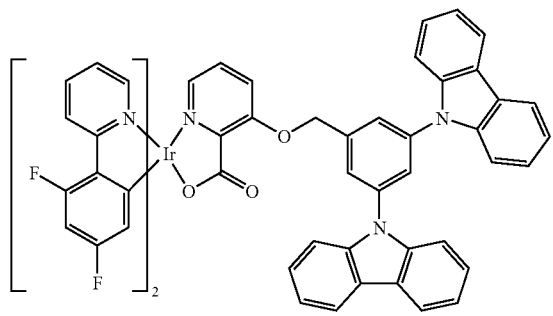
Formula 8
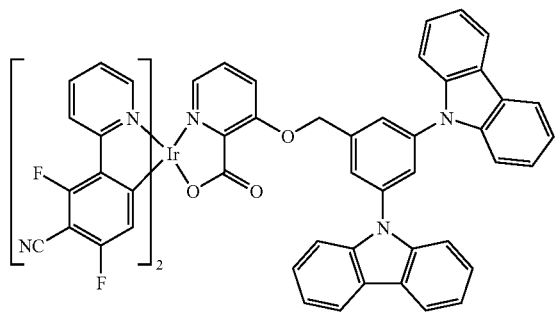
Formula 9
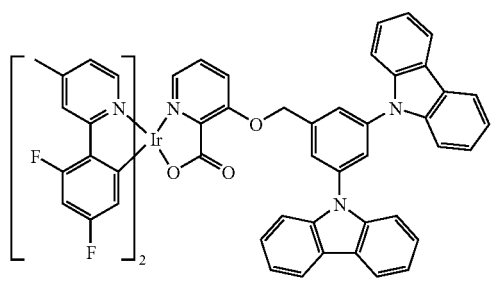
Formula 10
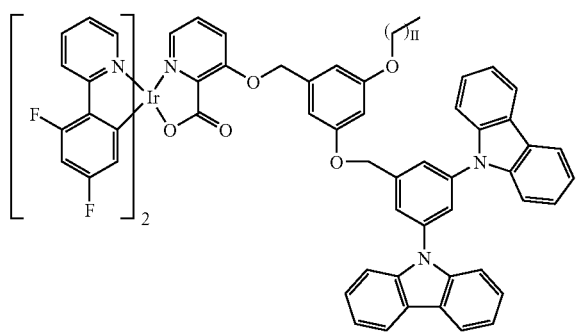
Formula 11
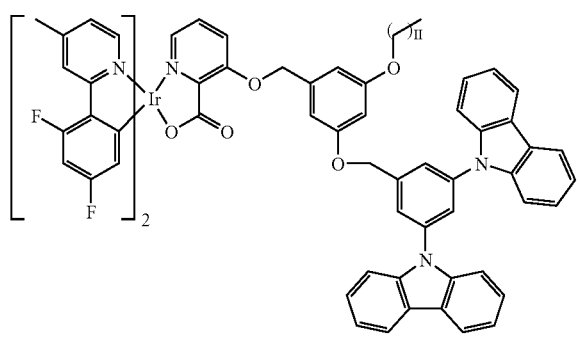
Formula 12
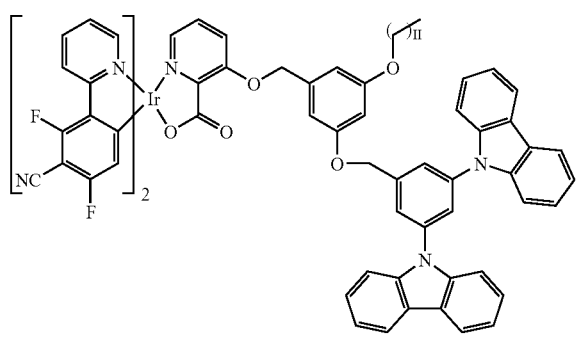
Formula 13
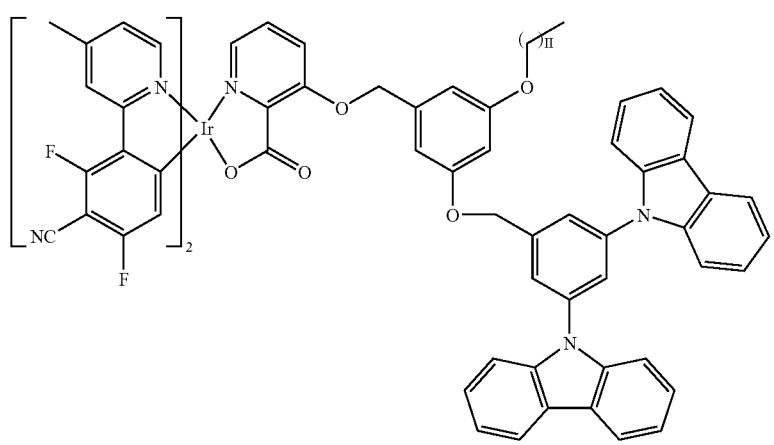

Formula 14

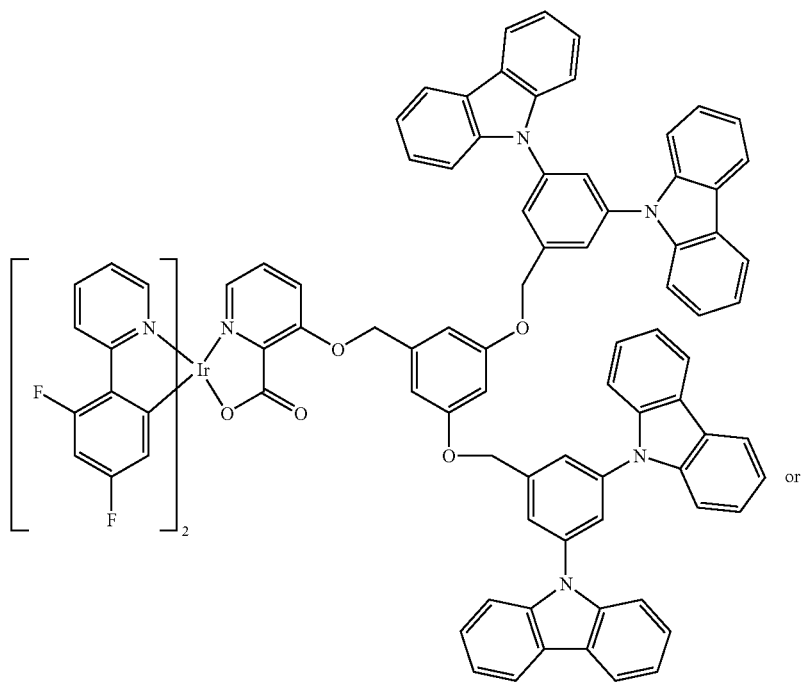

or

Formula 15

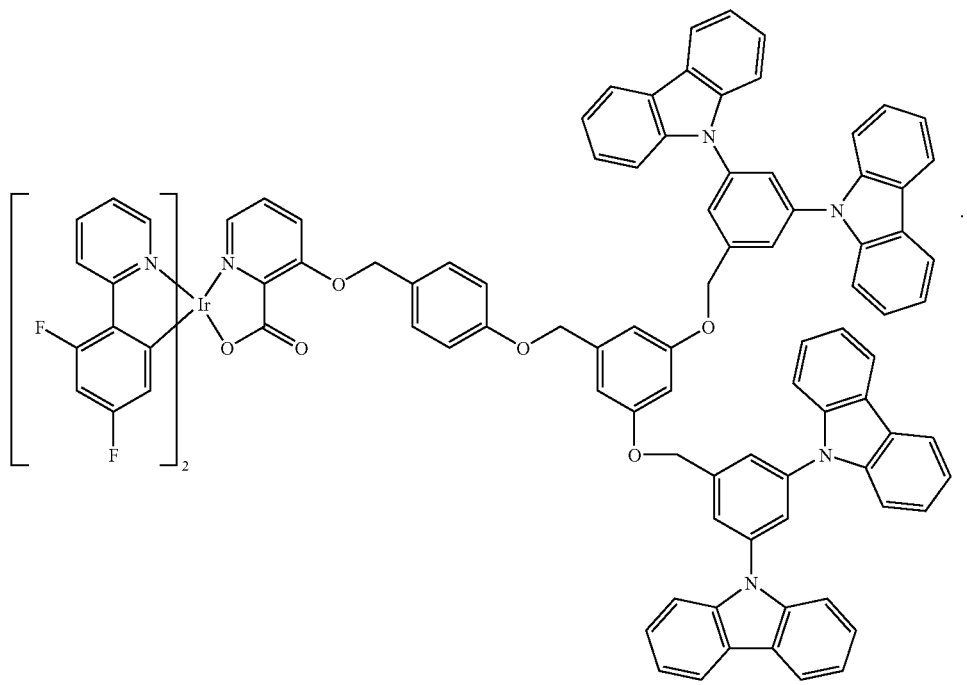

7. An organic electroluminescence device comprising a pair of electrodes and an organic layer between the pair of electrodes, wherein the organic layer contains the organic metal compound of claim 1.

8. The organic electroluminescence device as set forth in claim 7, wherein the organic layer is an emitting layer.

9. A preparation method for an organic electroluminescence device comprising the following steps:
forming a first electrode on substrate;
forming an organic layer on the first electrode;
and forming a second electrode on the organic layer, wherein the organic layer is formed by doping of the organic metal compound of claim 1.

10. The preparation method for the organic electroluminescence device as set forth in claim 9, wherein the first electrode is an anode, the second electrode is a cathode, and the organic layer is an emitting layer.

11. The preparation method for the organic electroluminescence device as set forth in claim 9, wherein the organic layer is formed by a wet process.

12. The preparation method of the organic electroluminescence device as set forth in claim 9, wherein the doping level is regulated by the number of the compounds for host to be connected to the compounds for dopant.

* * * * *